(12) United States Patent
Stamler

(10) Patent No.: US 11,576,900 B2
(45) Date of Patent: Feb. 14, 2023

(54) COMPOSITIONS AND METHODS OF REDUCING SERUM CHOLESTEROL AND PCSK9

(71) Applicant: CASE WESTERN RESERVE UNIVERSITY, Cleveland, OH (US)

(72) Inventor: Jonathan S. Stamler, Cleveland, OH (US)

(73) Assignees: CASE WESTERN RESERVE UNIVERSITY, Cleveland, OH (US); UNIVERSITY HOSPITALS CLEVELAND MEDICAL CENTER, Cleveland, OH (US)

( * ) Notice: Subject to any disclaimer, the term of this patent is extended or adjusted under 35 U.S.C. 154(b) by 0 days.

(21) Appl. No.: 16/648,737

(22) PCT Filed: Sep. 21, 2018

(86) PCT No.: PCT/US2018/052214
§ 371 (c)(1),
(2) Date: Mar. 19, 2020

(87) PCT Pub. No.: WO2019/060720
PCT Pub. Date: Mar. 28, 2019

(65) Prior Publication Data
US 2020/0268717 A1  Aug. 27, 2020

Related U.S. Application Data

(60) Provisional application No. 62/562,784, filed on Sep. 25, 2017.

(51) Int. Cl.
*A61K 31/4184* (2006.01)
*A61P 9/00* (2006.01)
*A61P 3/06* (2006.01)
*A61K 31/4174* (2006.01)
*A61K 31/4188* (2006.01)
*A61K 31/422* (2006.01)
*A61K 31/4245* (2006.01)

(52) U.S. Cl.
CPC ...... *A61K 31/4184* (2013.01); *A61K 31/4174* (2013.01); *A61K 31/4188* (2013.01); *A61K 31/422* (2013.01); *A61K 31/4245* (2013.01); *A61P 3/06* (2018.01)

(58) Field of Classification Search
CPC ............................ A61K 31/4184; A61P 9/00
See application file for complete search history.

(56) References Cited

U.S. PATENT DOCUMENTS

| 2,683,718 | A | 7/1954 | Dornfeld et al. |
| 4,436,745 | A | 3/1984 | York, Jr. |
| 5,153,211 | A | 10/1992 | York, Jr. |
| 7,674,795 | B2 | 3/2010 | Mailliet et al. |
| 10,117,842 | B2 | 11/2018 | Nagy |
| 10,537,557 | B2 | 1/2020 | Raffay et al. |
| 2010/0292178 | A1 | 11/2010 | Young |
| 2010/0305078 | A1 | 12/2010 | Schotzinger et al. |
| 2011/0092566 | A1 | 4/2011 | Srivastava et al. |
| 2012/0083501 | A1 | 4/2012 | Hunt et al. |
| 2012/0220001 | A1 | 8/2012 | Marliàre |
| 2013/0196342 | A1 | 8/2013 | Stamler et al. |
| 2014/0206693 | A1 | 7/2014 | Srivastava et al. |
| 2017/0360755 | A1 | 12/2017 | Stamler |

FOREIGN PATENT DOCUMENTS

| EP | 1961420 A1 | 8/2008 |
| EP | 1987829 A1 | 11/2008 |
| JP | 58-140020 A | 8/1983 |
| JP | 2004315409 A | 11/2004 |
| JP | 2006510379 A | 3/2006 |
| WO | 2002/047680 A2 | 6/2002 |
| WO | 2004/110488 A1 | 12/2004 |
| WO | 2008/118370 A2 | 10/2008 |
| WO | 2010/104595 A1 | 9/2010 |
| WO | 2016/090373 A1 | 6/2016 |
| WO | 2016090373 A1 | 6/2016 |

OTHER PUBLICATIONS

Barski et al. "Tho Aldo-Keto Reductase Superfamily and its Rult:, in Drug Metabolism and Detoxification" Drug Metabolism Reviews. Nov. 6, 2008 (Nov. 6, 2008), vol. 40, p. 553-624.
Fletcher, "What should my cholesterol level be at my age?" Medical News Today. Feb. 20, 2017 (Feb. 20, 2017) https://www.medicalnewstoday.com/articles/315900.php; p. 2, para 2.
Applicant: Case Western Reserve University; PCT International Application No. PCT/US19/52426, Filed: Sep. 23, 2019; PCT International Search Report and Written Opinion, Authorized Officer: Lee Young; Feb. 7, 2020; 9 pgs.
PubChem-CID-10335836, Create Date: Oct. 25, 2006; p. 2.
Hwang et al. The FASEB Journal, Published online Dec. 2001, pp. 1-22.
International Search Report & Written Opinion for International Application No. PCT/US2015/064308.
Jonathan S. Stamler; "Compositions and Methods of Reducing Serum Cholesterol and PCSK9"; U.S. Appl. No. 16/648,737, filed Mar. 19, 2020; U.S. Non-Final Office Action dated Mar. 7, 2022; 11 pgs.
Malatkova, Pet al., "Human Carbonyl Reductases", Current Drug Metabolism, vol. 11, 2010, 24 pp. 639-658.
Morakinyo, MK et al., "Detailed mechanistic investigation into the S-nitrosation of cysteamine", 26 Can. J. Chem. vol. 90, 2012, pp. 724-738.

(Continued)

*Primary Examiner* — Samira J Jean-Louis
(74) *Attorney, Agent, or Firm* — Tarolli, Sundheim, Covell & Tummino LLP

(57) ABSTRACT

A method of lowering cholesterol and/or PCSK9 levels in a subject in need thereof includes administering to the subject an ADH inhibitor, AKR inhibitor, and/or SNO-CoAR inhibitor at an amount(s) effective to reduce serum cholesterol and/or PCSK9 levels.

9 Claims, 14 Drawing Sheets

(56) References Cited

OTHER PUBLICATIONS

Morris, SL et al., "Inhibition of Bacillus cereus Spore Outgrowth by Covalent Modification of a Sulfhydryl Group by Nitrosothiol and Iodoacetate", Journal of Bacteriology, vol. 148, No. 2, Nov. 1981, pp. 465-471.

Partial Supplementary European Search Report for Application No. 15864966.5-1112/3226859.

PubChem CID 20267156, create date, Dec. 5, 2007 p. 2 formula.

PubChem CID 20267160, create date, Dec. 5, 2007 p. 1 formula.

Puneet Anand et al., "Identification of S-nitroso-CoA reductases that regulate protein S-nitrosylation", Proceedings of the National Academy of Sciences, vol. 111, No. 52, Dec. 15, 2014, pp. 8572-18577.

Puneet Anand, "Purification and Characterization of Novel Denitrosylases from Yeast and Mammals", Dec. 31, 2012, pp. 1-156.

Roediger, Wew. Review article: nitric oxide from dysbiotic bacterial respiration of nitrate in the pathogenesis and as a target for therapy of ulcerative colitis "Ailment Pharmacol", Ther. vol. 27, 2008, pp. 531-541.

Soda, Met al., "Inhibition of Human Aldose Reductase-Like Protein (AKR1B10) by alpha- and gamma-Mangostins, Major Components of Pericarps of Mangosteen", Biol Pharm. Bull. vol. 35, No. 11, 2012, pp. 2075-2080.

Supplemental European search report for application No. 15864966.5-1112/3226859, dated Nov. 30, 2018.

Suropean Search Report for application No. 15864966.5-1112/3226859.

Tao B et al: "Synthesis of Conformationally Constrained Spirohydantoins With a Dibenzoaa, Doheptadiene Ring", Synthesis, Georg Thieme Verlag, Stutigart, DE, No. 10, Feb. 29, 2000, pp. 1449-1453.

Zhang, HH et al., "Estrogen-Responsive nitroso-Proteorne in Uterine Artery Endothelial Cells: Role of Endothelial Nitric Oxide Synthase and Estrogen Receptor-beta", J Cell Physiol. vol. 227, No. 1, Jan. 2012, pp. 146-159.

Japanese Application No. 2020-516839; Japanese Office Action—Notice of Reasons for Rejection; dated Oct. 18, 2022; 15 pgs.

Kaukola, Sirkka, et al. "Effect of phenytoin on serum lipoproteins in middle-aged men." Journal of Cardiovascular Pharmacology 3.1 (1981): 207-214.

AKR1A1-deficient mice have reduced total serum cholesterol 12 week old male mice 18 hour fasting AKR1A1-deficient mice have reduced total serum cholesterol 24 week old male mice 6 hour fasting Cholesterol fractionation confirms reduced total serum cholesterol in AKR1A1-deficient mice 24 week old male mice 6 hour fasting AKR1A1-deficient mice have lower serum PCSK9

24 week old male mice 6 hour fasting

C57BL6J mice treated for 4 weeks with in-diet Imirestat display lower total serum cholesterol 20 week old male mice (24 weeks at sacrifice)

6 hour fasting

C57BL6J mice treated for 4 weeks with in-diet Imirestat display lower serum PCSK9

20 week old male mice (24 weeks at sacrifice)

6 hour fasting

ApoE-deficient mice treated for 4 weeks with in-diet Imirestat have lower total serum cholesterol 20 week old male mice (24 weeks at sacrifice)

6 hour fasting

ApoE-deficient mice treated for 4 weeks with in-diet Imirestat have lower serum PCSK9

20 week old male mice (24 weeks at sacrifice)

6 hour fasting

COMPOSITIONS AND METHODS OF REDUCING SERUM CHOLESTEROL AND PCSK9

RELATED APPLICATION

This application claims priority from U.S. Provisional Application No. 62/562,784, filed Sep. 25, 2017, the subject matter of which is incorporated herein by reference in its entirety.

TECHNICAL FIELD

This application relates to compositions and methods of lowering serum cholesterol and/or PCSK9 and particularly relates to the use of alcohol dehydrogenase inhibitors, aldoketo reductase inhibitors, and/or SNO-Coenzyme A reductase inhibitors in methods of reducing serum cholesterol and/or PCSK9 levels in a subject.

BACKGROUND

While the human body requires cholesterol for multifarious functions like building cell membranes, making hormones, and producing fat digestive compounds, excessive cholesterol increases a person's risk of developing heart disease. People with hypercholesterolemia have a high risk of developing a form of heart disease called "atherosclerotic heart disease" or "coronary artery disease" where excess cholesterol in the bloodstream is deposited in the walls of blood vessels, particularly in the arteries that supply blood to the heart (coronary arteries). The abnormal buildup of cholesterol forms clumps (plaque) that narrow and harden artery walls. As the clumps get bigger, they can clog the arteries and restrict the flow of blood to the heart. The buildup of plaque in coronary arteries causes a form of chest pain called angina and greatly increases a person's risk of having a heart attack. In general optimized cholesterol metabolism is required for healthy living.

Cholesterol travels through the bloodstream in small packages called lipoproteins. Several kinds of lipoproteins carry cholesterol throughout the body, primarily: low-density lipoproteins (LDL), high-density lipoproteins (HDL), and very low density lipoprotein (VLDL). Having healthy levels of both types of lipoproteins is important. LDL cholesterol sometimes is called "bad" cholesterol. A high LDL level leads to a buildup of cholesterol in arteries. HDL cholesterol sometimes is called "good" cholesterol. This is because it carries cholesterol from other parts of your body back to your liver. The liver then removes the cholesterol from your body. Effective therapeutic management methods for hypercholesterolemia aim to reduce LDL cholesterol (and VLDL) and increase levels of HDL cholesterol so that excess cholesterol may be removed efficiently from the body.

In the past two decades or so, the segregation of cholesterolemic compounds into HDL and LDL regulators and recognition of the desirability of decreasing blood levels of the latter has led to the development of a number of drugs. However, many of these drugs have undesirable side effects and/or are contraindicated in certain patients, particularly when administered in combination with other drugs.

Bile-acid-binding resins are a class of drugs that interrupt the recycling of bile acids from the intestine to the liver. Examples of bile-acid-binding resins are cholestyramine (QUESTRAN LIGHT, Bristol-Myers Squibb), and colestipol hydrochloride (COLESTID, Pharmacia & Upjohn Company). When taken orally, these positively charged resins bind to negatively charged bile acids in the intestine. Because the resins cannot be absorbed from the intestine, they are excreted, carrying the bile acids with them. The use of such resins, however, at best only lowers serum cholesterol levels by about 20%. Moreover, their use is associated with gastrointestinal side-effects, including constipation and certain vitamin deficiencies. Further, since the resins bind to drugs, other oral medications must be taken at least one hour before or four to six hours subsequent to ingestion of the resin, complicating heart patients' drug regimens.

Statins are inhibitors of cholesterol synthesis. Sometimes, statins are used in combination therapy with bile-acid-binding resins. Lovastatin (MEVACOR, Merck & Co., Inc.), a natural product derived from a strain of Aspergillus; pravastatin (PRAVACHOL, Bristol-Myers Squibb Co.); and atorvastatin (LIPITOR, Warner Lambert) block cholesterol synthesis by inhibiting HMGCoA reductase, the key enzyme involved in the cholesterol biosynthetic pathway. Lovastatin significantly reduces serum cholesterol and LDL-serum levels. However, serum HDL levels are only slightly increased following lovastatin administration. The mechanism of the LDL-lowering effect may involve both reduction of VLDL concentration and induction of cellular expression of LDL-receptor, leading to reduced production and/or increased catabolism of LDL. Side effects, including liver and kidney dysfunction are associated with the use of these drugs.

Nicotinic acid, also known as niacin, is a water-soluble vitamin B-complex used as a dietary supplement and anti-hyperlipidemic agent. Niacin diminishes the production of VLDL and is effective at lowering LDL. It is used in combination with bile-acid-binding resins. Niacin can increase HDL when administered at therapeutically effective doses; however, its usefulness is limited by side effects and questions of efficacy.

Fibrates are a class of lipid-lowering drugs used to treat various forms of hyperlipidemia, elevated serum triglycerides, which may also be associated with hypercholesterolemia. Fibrates appear to reduce the VLDL fraction and modestly increase HDL; however, the effects of these drugs on serum cholesterol is variable. In the United States, fibrates have been approved for use as antilipidemic drugs, but have not received approval as hypercholesterolemia agents. For example, clofibrate (ATROMID-S, Wyeth-Ayerst Laboratories) is an antilipidemic agent that acts to lower serum triglycerides by reducing the VLDL fraction. Although ATROMID-S may reduce serum cholesterol levels in certain patient subpopulations, the biochemical response to the drug is variable, and is not always possible to predict which patients will obtain favorable results. ATROMID-S has not been shown to be effective for prevention of coronary heart disease. The chemically and pharmacologically related drug, gemfibrozil (LOPID, Parke-Davis), is a lipid regulating agent which moderately decreases serum triglycerides and VLDL cholesterol. LOPED also increases HDL cholesterol, particularly the HDL2 and HDL3 subfractions, as well as both the AI/AII-HDL fractions. However, the lipid response to LOPID is heterogeneous, especially among different patient populations. Moreover, while prevention of coronary heart disease was observed in male patients between the ages of 40 and 55 without history or symptoms of existing coronary heart disease, it is not clear to what extent these findings can be extrapolated to other patient populations (e.g., women, older and younger males). Indeed, no efficacy was observed in patients with established coronary heart disease. Serious side-effects are associated with the use of fibrates, including toxicity; malignancy, particularly malignancy of gastrointestinal cancer; gallbladder disease; and an increased incidence in non-coronary mortality. These drugs are not indicated for the treatment of patients with high LDL or low HDL as their only lipid abnormality.

Oral estrogen replacement therapy may be considered for moderate hypercholesterolemia in post-menopausal women. However, increases in HDL may be accompanied with an increase in triglycerides. Estrogen treatment is, of course, limited to a specific patient population, postmenopausal women, and is associated with serious side effects, including induction of malignant neoplasms; gall bladder disease; thromboembolic disease; hepatic adenoma; elevated blood pressure; glucose intolerance; and hypercalcemia.

Long chain carboxylic acids, particularly long chain alpha,omega-dicarboxylic acids with distinctive substitution patterns, and their simple derivatives and salts, have been disclosed for treating atherosclerosis, obesity, and diabetes (See, e.g., Bisgaier et al., 1998, J. Lipid Res. 39:17-30, and references cited therein; International Patent Publication WO 98/30530; U.S. Pat. No. 4,689,344; International Patent Publication WO 99/00116; and U.S. Pat. No. 5,756,344). However, some of these compounds while having serum triglyceride and serum cholesterol-lowering activities, have no value for treatment of obesity and hypercholesterolemia (U.S. Pat. No. 4,689,344).

Proprotein convertase subtilisin/kexin type 9 (PCSK9) is a proprotein convertase belonging to the proteinase K subfamily of the secretory subtilase family The encoded protein is synthesized as a soluble zymogen that undergoes autocatalytic intramolecular processing in the endoplasmic reticulum. Evidence suggest that PCSK9 increases plasma LDL cholesterol by promoting degradation of the LDL receptor, which mediates LDL endocytosis in the liver, the major route of LDL clearance from circulation. The structure of PCSK9 protein shows that it has a signal sequence, followed by a prodomain, a catalytic domain that contains a conserved triad of residues (D186, H226 and S386), and a C-terminal domain. It is synthesized as a soluble 74-kDa precursor that undergoes autocatalytic cleavage in the ER, generating a 14-kDa prodomain and 60-kDa catalytic fragment. The autocatalytic activity has been shown to be required for secretion. After cleavage the prodomain remains tightly associated with the catalytic domain.

SUMMARY

Embodiments described herein relate to compositions and methods of modulating serum cholesterol and/or proprotein convertase subtilisin/kexin type 9 (PCSK9) levels in a subject in need thererof and particularly relates to the use of alcohol dehydrogenase (ADH) inhibitors (e.g., ADH6 inhibitors), aldoketo reductase (AKR) inhibitors (e.g., AKR1A1 inhibitors), and/or SNO-Coenzyme A reductase (SNO-CoAR) inhibitors (e.g., ADH6 inhibitors and AKR1A1 inhibitors) for reducing cholesterol and/or PCSK9 levels in a subject in need thereof.

In some embodiments, the ADH inhibitors, AKR inhibitors, and/or SNO-CoAR inhibitors can be administered to a subject at an amount effective to lower PCSK9 levels. PCSK9 increases plasma LDL cholesterol (LDL-C) by promoting degradation of the LDL receptor, which mediates LDL endocytosis in the liver, the major route of LDL clearance from circulation. Lowering of PCSK9 levels by administration of ADH inhibitors, AKR inhibitors, and/or SNO-CoAR to a subject in need thereof can: (i) reduce total serum cholesterol by at least about 5%, about 10%, about 20%, about 25%, about 30%, about 35%, about 40%, about 45%, about 50%, or more relative to predose level; (ii) reduce serum LDL-C at least about 5%, about 10%, about 20%, about 25%, about 30%, about 35%, about 40%, about 45%, about 50%, about 60%, about 65%, about 70%, about 75%, about 80%, or more relative to predose level; (iii) reduce serum triglyceride at least about 5%, about 10%, about 20%, about 25%, about 30%, about 35%, about 40%, about 45%, about 50% relative to predose level; and/or (iv) not reduce serum HDL-C or reduces serum HDL-C no more than about 5%, about 10%, about 20%, about 25%, about 30% relative to predose level.

In some embodiments, the subject can have or be at risk of hypercholesterolemia, mixed dyslipidemia, atherosclerosis, a risk of developing atherosclerosis, coronary heart disease, a history of coronary heart disease, early onset coronary heart disease, acute coronary syndrome, one or more risk factors for coronary heart disease, type I diabetes, type II diabetes, type II diabetes with dyslipidemia, dyslipidemia, hypertriglyceridemia, hyperlipidemia, hyperfattyacidemia, hepatic steatosis, non-alcoholic steatohepatitis, or non-alcoholic fatty liver disease.

In certain embodiments, the ADH inhibitors, AKR inhibitors, and/or SNO-CoAR inhibitors administered to the subject do not lower or do not substantially lower HDL-C levels. In certain embodiments, the methods do not result in accumulation of lipids in the liver.

Other embodiments described herein relate to methods for decreasing LDL-C levels, or alternatively methods for treating hypercholesterolemia, by administering to an individual suffering from elevated LDL-C levels a therapeutically effective amount of an ADH inhibitor, AKR inhibitor, and/or SNO-CoAR inhibitor. In another embodiment, a method of decreasing LDL-C levels comprises selecting an individual in need of a decrease in LDL-C levels, and administering to the individual a therapeutically effective amount of an ADH inhibitor, AKR inhibitor, and/or SNO-CoAR inhibitor. In a further embodiment, a method of reducing coronary heart disease risk includes selecting an individual having elevated LDL-C levels and one or more additional indicators of coronary heart disease risk, and administering to the individual a therapeutically effective amount of an ADH inhibitor, AKR inhibitor, and/or SNO-CoAR inhibitor.

In other embodiments, the LDL-C level in the subject can be from 30 to 70 mg/dL, 70 to 100 mg/dL, 100 to 129 mg/dL, from 130 to 159 mg/dL, from 160 to 189 mg/dL, or greater than or equal to 190 mg/dL.

In one embodiment, administration of a therapeutically effective amount of an ADH inhibitor, AKR inhibitor, and/or SNO-CoAR inhibitor is accompanied by monitoring of LDL-C levels in the serum of an individual, to determine an individual's response to administration of the ADH inhibitor, AKR inhibitor, and/or SNO-CoAR inhibitor. An individual's response to administration of the ADH inhibitor, AKR inhibitor, and/or SNO-CoAR inhibitor can be used by a physician to determine the amount and duration of therapeutic intervention.

In one embodiment, administration of an ADH inhibitor, AKR inhibitor, and/or SNO-CoAR inhibitor results in LDL-C levels below 190 mg/dL, below 160 mg/dL, below 130 mg/dL, below 100 mg/dL, below 70 mg/dL, below 50 mg/dL, below 30 mg/dL. In another embodiment, administration of an ADH inhibitor, AKR inhibitor, and/or SNO-CoAR inhibitor decreases LDL-C by at least 15%, by at least 25%, by at least 50%, by at least 60%, by at least 70%, by at least 75%, by at least 80%, by at least 85%, by at least 90%, or by at least 95%.

An individual having elevated LDL-C levels may also exhibit reduced HDL-C levels and/or elevated total cholesterol levels. Accordingly, in one embodiment a therapeutically effective amount of an ADH inhibitor, AKR inhibitor, and/or SNO-CoAR inhibitor is administered to an individual having elevated LDL-C levels, who also has reduced HDL-C levels and/or elevated total cholesterol levels.

Individuals having elevated LDL-C levels may also exhibit elevated triglyceride levels. Accordingly, in one embodiment a therapeutically effective amount of an ADH inhibitor, AKR inhibitor, and/or SNO-CoAR inhibitor is administered to an individual having elevated LDL-C levels, and also having elevated triglyceride levels.

DETAILED DESCRIPTION

Figure 1:
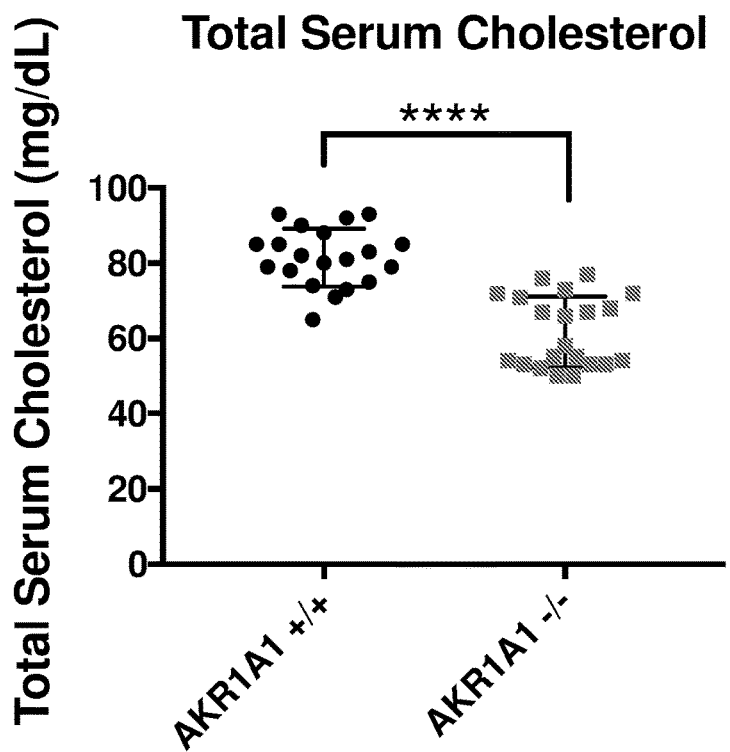
FIG. 1 illustrates a graph showing total serum cholesterol levels in AKR1A1 deficient 12-week mice compared to 12-week wild-type mice.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

The term "hypercholesterolemia" means a condition characterized by elevated serum cholesterol.

The term "hyperlipidemia" means a condition characterized by elevated serum lipids.

The term "hypertriglyceridemia" means a condition characterized by elevated serum triglyceride levels.

The term "non-familial hypercholesterolemia" means a condition characterized by elevated serum cholesterol that is not the result of a single gene mutation.

The term "polygenic hypercholesterolemia" means a condition characterized by elevated cholesterol that results from the influence of a variety of genetic factors. In certain embodiments, polygenic hypercholesterolemia may be exacerbated by dietary intake of lipids.

The term "familial hypercholesterolemia (FH)" means an autosomal dominant metabolic disorder characterized by a mutation in the LDL-receptor (LDL-R) gene, markedly elevated LDL-C and premature onset of atherosclerosis. A diagnosis of familial hypercholesterolemia is made when an individual meets one or more of the following criteria: genetic testing confirming 2 mutated LDL-receptor genes; genetic testing confirming one mutated LDL-receptor gene; document history of untreated serum LDL-cholesterol greater than 500 mg/dL; tendinous and/or cutaneous xanthoma prior to age 10 years; or, both parents have documented elevated serum LDL-cholesterol prior to lipid-lowering therapy consistent with heterozygous familial hypercholesterolemia.

The term "homozygous familial hypercholesterolemia" or "HoFH" means a condition characterized by a mutation in both maternal and paternal LDL-R genes.

The term "heterozygous familial hypercholesterolemia" or "HeFH" means a condition characterized by a mutation in either the maternal or paternal LDL-R gene.

The term "mixed dyslipidemia" means a condition characterized by elevated serum cholesterol and elevated serum triglycerides.

The term "diabetic dyslipidemia" or "Type II diabetes with dyslipidemia" means a condition characterized by Type II diabetes, reduced HDL-C, elevated serum triglycerides, and elevated small, dense LDL particles.

The term "CHD risk equivalents," means indicators of clinical atherosclerotic disease that confer a high risk for coronary heart disease, and include clinical coronary heart disease, symptomatic carotid artery disease, peripheral arterial disease, and/or abdominal aortic aneurysm.

The term "metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL.

The term "Non-alcoholic fatty liver disease (NAFLD)" means a condition characterized by fatty inflammation of the liver that is not due to excessive alcohol use (for example, alcohol consumption of over 20 g/day). In certain embodiments, NAFLD is related to insulin resistance and the metabolic syndrome.

The term "Non-alcoholic steatohepatitis (NASH)" means a condition characterized by inflammation and the accumulation of fat and fibrous tissue in the liver, that is not due to excessive alcohol use. NASH is an extreme form of NAFLD.

The term "Major risk factors" mean factors that contribute to a high risk for coronary heart disease, and include without limitation cigarette smoking, hypertension, low HDL-C, family history of coronary heart disease, and age.

The term "CHD risk factors" mean CHD risk equivalents and major risk factors.

The term "Coronary heart disease (CHD)" means a narrowing of the small blood vessels that supply blood and oxygen to the heart, which is often a result of atherosclerosis.

The term "reduced coronary heart disease risk" means a reduction in the likelihood that an individual will develop coronary heart disease. In certain embodiments, a reduction in coronary heart disease risk is measured by an improvement in one or more CHD risk factors, for example, a decrease in LDL-C levels.

The term "atherosclerosis" means a hardening of the arteries affecting large and medium-sized arteries and is characterized by the presence of fatty deposits. The fatty deposits are called "atheromas" or "plaques," which consist mainly of cholesterol and other fats, calcium and scar tissue, and damage the lining of arteries.

The term "history of coronary heart disease" means the occurrence of clinically evident coronary heart disease in the medical history of an individual or an individual's family member.

The term "early onset coronary heart disease" means a diagnosis of coronary heart disease prior to age 50.

The term "statin intolerant individual" means an individual who as a result of statin therapy experiences one or more of creatine kinase increases, liver function test abnormalities, muscle aches, or central nervous system side effects.

The term "efficacy" means the ability to produce a desired effect. For example, efficacy of a lipid-lowering therapy may be reduction in the concentration of one or more of LDL-C, VLDL-C, IDL-C, non-HDL-C, ApoB, lipoprotein(a), or triglycerides.

The term "acceptable safety profile" means a pattern of side effects that is within clinically acceptable limits.

The term "lipid-lowering therapy" means a therapeutic regimen provided to an individual to reduce one or more lipids in a individual. In certain embodiments, a lipid-lowering therapy is provide to reduce one or more of ApoB, total cholesterol, LDL-C, VLDL-C, IDL-C, non-HDL-C, triglycerides, small dense LDL particles, and Lp(a) in a individual.

The term "lipid-lowering agent" means a pharmaceutical agent provided to an individual to achieve a lowering of lipids in the individual. For example, in certain embodiments, a lipid-lowering agent is provided to an individual to reduce one or more of ApoB, LDL-C, total cholesterol, and triglycerides.

The term "LDL-C target" means an LDL-C level that is desired following lipid-lowering therapy.

The term "Low LDL-receptor activity" means LDL-receptor activity that is not sufficiently high to maintain clinically acceptable levels of LDL-C in the bloodstream.

The term "cardiovascular outcome" means the occurrence of major adverse cardiovascular events.

The term "improved cardiovascular outcome" means a reduction in the occurrence of major adverse cardiovascular events, or the risk thereof. Examples of major adverse cardiovascular events include, without limitation, death, reinfarction, stroke, cardiogenic shock, pulmonary edema, cardiac arrest, and atrial dysrhythmia.

The term "surrogate markers of cardiovascular outcome" means indirect indicators of cardiovascular events, or the risk thereof. For example, surrogate markers of cardiovascular outcome include carotid intimal media thickness (CIMT). Another example of a surrogate marker of cardiovascular outcome includes atheroma size. Atheroma size may be determined by intravascular ultrasound (IVUS). Surrogate markers also include increased HDL-cholesterol, or any combination of the markers above.

The term "increased HDL-C" means an increase in serum HDL-C in an individual over time.

The term "lipid-lowering" means a reduction in one or more serum lipids in an individual over time.

The term "co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses administration in parallel or sequentially.

"Administered concomitantly" refers to the administration of two agents at the same therapeutic time frame, in any manner in which the pharmacological effects of both are manifest in the patient at the same time. Concomitant administration does not require that both agents be administered in a single pharmaceutical composition, in the same dosage form, or by the same route of administration.

The term "statin" means a pharmaceutical agent that inhibits the activity of HMG-CoA reductase.

The term "HMG-CoA reductase inhibitor" means a pharmaceutical agent that acts through the inhibition of the enzyme HMG-CoA reductase.

The term "cholesterol absorption inhibitor" means a pharmaceutical agent that inhibits the absorption of exogenous cholesterol obtained from diet.

The term "LDL apheresis" means a form of apheresis by which LDL-C is removed from blood. Typically, an individual's blood is removed from a vein, and separated into red cells and plasma. LDL-C is filtered out of the plasma prior to return of the plasma and red blood cells to the individual.

The term "MTP inhibitor" means a pharmaceutical agent that inhibits the enzyme microsomal triglyceride transfer protein.

The term "Low density lipoprotein-cholesterol (LDL-C)" means cholesterol carried in low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

The term "Very low density lipoprotein-cholesterol (VLDL-C)" means cholesterol associated with very low density lipoprotein particles. Concentration of VLDL-C in serum (or plasma) is typically quantified in mg/dL or nmol/L. "Serum VLDL-C" and "plasma VLDL-C" mean VLDL-C in the serum or plasma, respectively.

The term "Intermediate low density lipoprotein-cholesterol (IDL-C)" means cholesterol associated with intermediate density lipoprotein. Concentration of IDL-C in serum (or plasma) is typically quantified in mg/dL or nmol/L. "Serum IDL-C" and "plasma IDL-C" mean IDL-C in the serum or plasma, respectively.

The term "Non-high density lipoprotein-cholesterol (Non-HDL-C)" means cholesterol associated with lipoproteins other than high density lipoproteins, and includes, without limitation, LDL-C, VLDL-C, and IDL-C.

The term "High density lipoprotein-C(HDL-C)" means cholesterol associated with high density lipoprotein particles. Concentration of HDL-C in serum (or plasma) is typically quantified in mg/dL or nmol/L. "Serum HDL-C" and "plasma HDL-C" mean HDL-C in the serum and plasma, respectively.

The term "Total cholesterol" means all types of cholesterol, including, but not limited to, LDL-C, HDL-C, IDL-C and VLDL-C. Concentration of total cholesterol in serum (or plasma) is typically quantified in mg/dL or nmol/L.

The term "Lipoprotein(a)" or "Lp(a)" means a lipoprotein particle that is comprised of LDL-C, an apolipoprotein(a) particle, and an apolipoproteinB-100 particle.

The term"ApoA1" means apolipoprotein-A1 protein in serum. Concentration of ApoA1 in serum is typically quantified in mg/dL or nmol/L.

The "ApoB:ApoA1 ratio" means the ratio of ApoB concentration to ApoA1 concentration.

The term "ApoB-containing lipoprotein" means any lipoprotein that has apolipoprotein B as its protein component, and is understood to include LDL, VLDL, IDL, and lipoprotein(a).

The term "triglycerides" means lipids that are the triesters of glycerol. "Serum triglycerides" mean triglycerides present in serum. "Liver triglycerides" mean triglycerides present in liver tissue.

The term "serum lipids" mean cholesterol and triglycerides in the serum.

The term "elevated total cholesterol" means total cholesterol at a concentration in an individual at which lipid-lowering therapy is recommended, and includes, without limitation, elevated LDL-C", "elevated VLDL-C," "elevated IDL-C," and "elevated non-HDL-C." In certain embodiments, total cholesterol concentrations of less than 200 mg/dL, 200-239 mg/dL, and greater than 240 mg/dL are considered desirable, borderline high, and high, respectively. In certain embodiments, LDL-C concentrations of 100 mg/dL, 100-129 mg/dL, 130-159 mg/dL, 160-189 mg/dL, and greater than 190 mg/dL are considered optimal, near optimal/above optimal, borderline high, high, and very high, respectively.

The term "elevated triglyceride" means concentrations of triglyceride in the serum or liver at which lipid-lowering therapy is recommended, and includes "elevated serum triglyceride" and "elevated liver triglyceride." In certain embodiments, serum triglyceride concentration of 150-199 mg/dL, 200-499 mg/dL, and greater than or equal to 500 mg/dL is considered borderline high, high, and very high, respectively.

The term "elevated small LDL particles" means a concentration of small LDL particles in an individual at which lipid-lowering therapy is recommended.

The term "elevated small VLDL particles" means a concentration of small VLDL particles in an individual at which lipid-lowering therapy is recommended.

The term "elevated lipoprotein(a)" means a concentration of lipoprotein(a) in an individual at which lipid-lowering therapy is recommended.

The term "low HDL-C" means a concentration of HDL-C in an individual at which lipid-lowering therapy is recommended. In certain embodiments lipid-lowering therapy is recommended when low HDL-C is accompanied by elevations in non-HDL-C and/or elevations in triglyceride. In certain embodiments, HDL-C concentrations of less than 40 mg/dL are considered low. In certain embodiments, HDL-C concentrations of less than 50 mg/dL are considered low.

The term "LDL/HDL ratio" means the ratio of LDL-C to HDL-C.

The term "Oxidized-LDL" or "Ox-LDL-C" means LDL-C that is oxidized following exposure to free radicals.

The term "individual having elevated LDL-C levels" means an individual who has been identified by a medical professional (e.g., a physician) as having LDL-C levels near or above the level at which therapeutic intervention is recommended, according to guidelines recognized by medical professionals. Such an individual may also be considered "in need of treatment" to decrease LDL-C levels.

"Cholesterol related disorders" (which include "serum cholesterol related disorders") include any one or more of the following: hypercholesterolemia, hperlipidemia, heart disease, metabolic syndrome, diabetes, coronary heart disease, stroke, cardiovascular diseases, Alzheimer's disease and generally dyslipidemias, which can be manifested, for example, by an elevated total serum cholesterol, elevated LDL, elevated triglycerides, elevated VLDL, and/or low HDL. Hypercholesterolemia is, in fact, an established risk factor for coronary heart disease (CHD) in humans. Lowering of low-density lipoprotein cholesterol (LDL-C) results in a reduction of cardiovascular risk and is a primary goal in pharmacotherapy for CHD. Statins (hydroxymethylglutaryl coenzyme A [HMG CoA] reductase inhibitors) are currently the treatment of choice for hypercholesterolemia. However, emerging data indicate that more aggressive treatment of hypercholesterolemia is associated with lower risk for CHD events. In addition, a subset of patients are intolerant to, or do not respond adequately to, statin therapy. Thus, novel therapies that can be used alone or in combination with existing agents to more effectively reduce LDL-C may be useful.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analogue" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, $-CF_3$, or $-CN$, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate. The term sulfoxide refers to a sulfur attached to 2 different carbon atoms and one oxygen and the S—O bond can be graphically represented with a double bond (S=O), a single bond without charges (S—O) or a single bond with charges [S(+)—O(-)].

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—ON$^+$C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

The terms "healthy" and "normal" are used interchangeably herein to refer to a subject or particular cell or tissue that is devoid (at least to the limit of detection) of a disease condition.

Embodiments described herein relate to compositions and methods of modulating serum cholesterol and/or proprotein convertase subtilisin/kexin type 9 (PCSK9) levels in a subject in need thereof and particularly relates to the use of alcohol dehydrogenase (ADH) inhibitors (e.g., ADH6 inhibitors), aldoketo reductase (AKR) inhibitors (e.g., AKR1A1 inhibitors and/or AKR1B1 inhibitors), and/or SNO-Coenzyme A reductase (SNO-CoAR) inhibitors (e.g., ADH6 inhibitors and AKR1A1 inhibitors) for reducing cholesterol and/or PCSK9 levels in a subject in need thereof.

Elevated levels of LDL-cholesterol (HDL-C) are recognized as a major independent risk factor for coronary heart disease (CHD). Even in individuals undergoing aggressive treatment with currently available cholesterol-lowering agents to reduce LDL-cholesterol (LDL-C) levels, coronary events still occur, and elevated LDL-C levels remain a major risk factor for coronary heart disease in these individuals. Furthermore, many individuals undergoing LDL-lowering therapy do not reach their target LDL-C levels, and thus remain at risk for CHD. Accordingly, there is a need for additional LDL-C lowering agents.

As illustrated in FIGS. 1-15, it was found that AKR inhibitors, such as selective and/or partially selective AKR1A1 inhibitors (e.g., Imirestat) and/or AKR1B1 inhibitors, can be used to reduce cholesterol and/or PCSK9 levels in a subject in need thereof and therefore are useful for the treatment of hypercholesterolemia. Treatment of hypercholesterolemia with the ADH inhibitors, AKR inhibitors, and/or SNO-CoAR inhibitors encompasses a therapeutic regimen that results in a clinically desirable outcome. For example, the ADH inhibitors, AKR inhibitors, and/or SNO-CoAR inhibitors can be administered to a subject for the treatment of elevated cholesterol, such as elevated LDL-C. In addition, the ADH inhibitors, AKR inhibitors, and/or SNO-CoAR inhibitors can be administered to a subject to reduce the risk of CHD, in subjects exhibiting one or more risk factors for CHD. Furthermore, the ADH inhibitors, AKR inhibitors, and/or SNO-CoAR inhibitors can be administered to a subject to treat and/or prevent atherosclerosis.

Moreover, LDL receptor (LDLR) expression regulates cholesterol levels. Higher LDLR correlates with lower serum cholesterol in a subject. LDLR can be regulated by two mechanism, PCSK9 and IDOL (E3 Ligase). PCSK9 increases plasma LDL cholesterol by promoting degradation of the LDLR, which mediates LDL endocytosis in the liver, the major route of LDL clearance from circulation. Inhibition of AKR1A1 lowers PCSK9 levels in plasma and causes IDOL inhibition and degradation in the liver, resulting in increased LDLR expression and lower serum LDL cholesterol.

Thus, in some embodiments, ADH inhibitors, AKR inhibitors, and/or SNO-CoAR inhibitors can be administered to a subject at an amount effective to lower PCSK9 levels. Lowering of PCSK9 levels by administration of ADH inhibitors, AKR inhibitors, and/or SNO-CoAR to a subject in need thereof can: (i) reduce total serum cholesterol by at least about 5%, about 10%, about 20%, about 25%, about 30%, about 35%, about 40%, about 45%, about 50%, or more relative to predose level; (ii) reduce serum LDL-C cholesterol at least about 5%, about 10%, about 20%, about 25%, about 30%, about 35%, about 40%, about 45%, about 50%, about 60%, about 65%, about 70%, about 75%, about 80%, or more relative to predose level; (iii) reduce serum triglyceride at least about 5%, about 10%, about 20%, about 25%, about 30%, about 35%, about 40%, about 45%, about 50% relative to predose level; and/or (iv) not reduce serum HDL-C or reduces serum HDL-C no more than about 5%, about 10%, about 20%, about 25%, about 30% relative to predose level.

In some embodiments, the subject can have hypercholesterolemia, mixed dyslipidemia, atherosclerosis, a risk of developing atherosclerosis, coronary heart disease, a history of coronary heart disease, early onset coronary heart disease, acute coronary syndrome, one or more risk factors for coronary heart disease, type II diabetes, type II diabetes with dyslipidemia, dyslipidemia, hypertriglyceridemia, hyperlipidemia, hyperfattyacidemia, hepatic steatosis, non-alcoholic steatohepatitis, or non-alcoholic fatty liver disease.

In certain embodiments, the ADH inhibitors, AKR inhibitors, and/or SNO-CoAR inhibitors administered to the subject do not lower or do not substantially lower HDL-C levels. In certain embodiments, the methods described herein do not result in accumulation of lipids in the liver.

Other embodiments described herein relate to methods for decreasing LDL-C levels, or alternatively methods for treating hypercholesterolemia, by administering to a subject suffering from elevated LDL-C levels a therapeutically effective amount of an ADH inhibitor, AKR inhibitor, and/or SNO-CoAR inhibitor. In another embodiment, a method of decreasing LDL-C levels comprises selecting an individual in need of a decrease in LDL-C levels, and administering to the individual a therapeutically effective amount of an ADH inhibitor, AKR inhibitor, and/or SNO-CoAR inhibitor. In a further embodiment, a method of reducing coronary heart disease risk includes selecting an individual having elevated LDL-C levels and one or more additional indicators of coronary heart disease risk, and administering to the individual a therapeutically effective amount of of an ADH inhibitor, AKR inhibitor, and/or SNO-CoAR inhibitor.

In other embodiments, the LDL-C level can be from 30 to 70 mg/dL, 70 to 100 mg/dL, 100 to 129 mg/dL, from 130 to 159 mg/dL, from 160 to 189 mg/dL, or greater than or equal to 190 mg/dL.

In one embodiment, administration of a therapeutically effective amount of an ADH inhibitor, AKR inhibitor, and/or SNO-CoAR inhibitor is accompanied by monitoring of LDL-C levels in the serum of an individual, to determine an individual's response to administration of the ADH inhibitor, AKR inhibitor, and/or SNO-CoAR inhibitor. An individual's response to administration of the ADH inhibitor, AKR inhibitor, and/or SNO-CoAR inhibitor is used by a physician to determine the amount and duration of therapeutic intervention.

In one embodiment, administration of an ADH inhibitor, AKR inhibitor, and/or SNO-CoAR inhibitor results in LDL-C levels below 190 mg/dL, below 160 mg/dL, below 130 mg/dL, below 100 mg/dL, below 70 mg/dL, or below 50 mg/dL. In another embodiment, administration of an ADH inhibitor, AKR inhibitor, and/or SNO-CoAR inhibitor decreases LDL-C by at least 15%, by at least 25%, by at least 50%, by at least 60%, by at least 70%, by at least 75%, by at least 80%, by at least 85%, by at least 90%, or by at least 95%.

An individual having elevated LDL-C levels may also exhibit reduced HDL-C levels and/or elevated total cholesterol levels. Accordingly, in one embodiment a therapeutically effective amount of an ADH inhibitor, AKR inhibitor, and/or SNO-CoAR inhibitor is administered to an individual having elevated LDL-C levels, who also has reduced HDL-C levels and/or elevated total cholesterol levels.

Individuals having elevated LDL-C levels may also exhibit elevated triglyceride levels. Accordingly, in one embodiment a therapeutically effective amount of of an ADH inhibitor, AKR inhibitor, and/or SNO-CoAR inhibitor is administered to an individual having elevated LDL-C levels, and also having elevated triglyceride levels.

Atherosclerosis can lead to coronary heart disease, stroke, or peripheral vascular disease. Elevated LDL-C levels are considered a risk factor in the development and progression of atherosclerosis. Accordingly, in one embodiment, a therapeutically effective amount of an ADH inhibitor, AKR inhibitor, and/or SNO-CoAR inhibitor can be administered to an individual having atherosclerosis. In a further embodiment, a therapeutically effective amount of an ADH inhibitor, AKR inhibitor, and/or SNO-CoAR inhibitor can be administered to an individual susceptible to atherosclerosis. Atherosclerosis is assessed directly through routine imaging techniques, such as ultrasound imaging techniques that reveal carotid intimomedial thickness. Accordingly, treatment and/or prevention of atherosclerosis further include monitoring atherosclerosis through routine imaging techniques. In one embodiment, administration of an ADH inhibitor, AKR inhibitor, and/or SNO-CoAR inhibitor leads to a lessening of the severity of atherosclerosis, as indicated by, for example, a reduction of carotid intimomedial thickness in arteries.

Measurements of cholesterol, lipoproteins and triglycerides are obtained using serum or plasma collected from an individual. Methods of obtaining serum or plasma samples are routine, as are methods of preparation of the serum samples for analysis of cholesterol, triglycerides, and other serum markers.

A physician may determine the need for therapeutic intervention for individuals in cases where more or less aggressive LDL-lowering therapy is needed. The practice of the methods herein may be applied to any altered guidelines provided by the National Cholesterol Education Program (NCEP), or other entities that establish guidelines for physicians used in treating any of the diseases or conditions listed herein, for determining coronary heart disease risk and diagnosing metabolic syndrome.

In certain embodiments, a pharmaceutical composition comprising an ADH inhibitor, AKR inhibitor, and/or SNO-CoAR inhibitor is for use in therapy. In certain embodiments, the therapy is the reduction of LDL-C, ApoB, VLDL-C, IDL-C, non-HDL-C, Lp(a), serum triglyceride, liver triglyceride, Ox-LDL-C, small LDL particles, small VLDL, phospholipids, or oxidized phospholipids in an individual. In certain embodiments, the therapy is the treatment of hypercholesterolemia, mixed dyslipidemia, atherosclerosis, a risk of developing atherosclerosis, coronary heart disease, acute coronary syndrome, a history of coronary heart disease, early onset coronary heart disease, one or more risk factors for coronary heart disease, type I diabetes, type II diabetes, type II diabetes with dyslipidemia, dyslipidemia, hypertriglyceridemia, hyperlipidemia, hyperfattyacidemia, hepatic steatosis, non-alcoholic steatohepatitis, or non-alcoholic fatty liver disease, peripheral vascular disease and stroke. In additional embodiments, the therapy is the reduction of CHD risk. In certain aspects, the therapy is prevention of atherosclerosis. In certain embodiments, the therapy is the prevention of coronary heart disease.

In certain embodiments, a pharmaceutical composition comprising an ADH inhibitor, AKR inhibitor, and/or SNO-CoAR inhibitor is used for the preparation of a medicament for reducing LDL-C, ApoB, VLDL-C, IDL-C, non-HDL-C, Lp(a), serum triglyceride, liver triglyceride, Ox-LDL-C, small LDL particles, small VLDL, phospholipids, or oxidized phospholipids in an individual. In certain embodiments pharmaceutical composition comprising an ADH inhibitor, AKR inhibitor, and/or SNO-CoAR inhibitor is used for the preparation of a medicament for reducing coronary heart disease risk. In certain embodiments, an ADH inhibitor, AKR inhibitor, and/or SNO-CoAR inhibitor is used for the preparation of a medicament for the treatment of hypercholesterolemia, mixed dyslipidemia, atherosclerosis, a risk of developing atherosclerosis, coronary heart disease, a history of coronary heart disease, early onset coronary heart disease, one or more risk factors for coronary heart disease, type I diabetes, type II diabetes, type II diabetes with dyslipidemia, dyslipidemia, hypertriglyceridemia, hyperlipidemia, hyperfattyacidemia, hepatic steatosis, non-alcoholic steatohepatitis, or non-alcoholic fatty liver disease, peripheral vascular disease, and stroke.

As will be appreciated by one of skill in the art, the ADH inhibitor, AKR inhibitor, and/or SNO-CoAR inhibitor can be therapeutically useful in treating and/or preventing cholesterol related disorders. In some embodiments, a "cholesterol related disorder" (which includes "serum cholesterol related disorders") includes any one or more of the following: familial hypercholesterolemia, non-familial hypercholesterolemia, hyperlipidemia, heart disease, metabolic syndrome, diabetes, coronary heart disease, stroke, cardiovascular diseases, Alzheimer's disease and generally dyslipidemias, which can be manifested, for example, by an elevated total serum cholesterol, elevated LDL, elevated triglycerides, elevated VLDL, and/or low HDL. Some non-limiting examples of primary and secondary dyslipidemias that can be treated using an ADH inhibitor, AKR inhibitor, and/or SNO-CoAR inhibitor, either alone, or in combination with one or more other agents include the metabolic syndrome, diabetes mellitus, familial combined hyperlipidemia, familial hypertriglyceridemia, familial hypercholesterolemias, including heterozygous hypercholesterolemia, homozygous hypercholesterolemia, familial defective apoplipoprotein B-100; polygenic hypercholesterolemia; remnant removal disease, hepatic lipase deficiency; dyslipidemia secondary to any of the following: dietary indiscretion, hypothyroidism, drugs including estrogen and progestin therapy, beta-blockers, and thiazide diuretics; nephrotic syndrome, chronic renal failure, Cushing's syndrome, primary biliary cirrhosis, glycogen storage diseases, hepatoma, cholestasis, acromegaly, insulinoma, isolated growth hormone deficiency, and alcohol-induced hypertriglyceridemia.

The ADH inhibitor, AKR inhibitor, and/or SNO-CoAR inhibitor can also be useful in preventing or treating atherosclerotic diseases, such as, for example, cardiovascular death, non-cardiovascular or all-cause death, coronary heart disease, coronary artery disease, peripheral arterial disease, stroke (ischaemic and hemorrhagic), angina pectoris, or cerebrovascular disease and acute coronary syndrome, myocardial infarction and untable angina. In some embodiments, the ADH inhibitor, AKR inhibitor, and/or SNO-CoAR inhibitor is useful in reducing the risk of: fatal and nonfatal heart attacks, fatal and non-fatal strokes, certain types of heart surgery, hospitalization for heart failure, chest pain in patients with heart disease, and/or cardiovascular events because of established heart disease such as prior heart attack, prior heart surgery, and/or chest pain with evidence of clogged arteries and/or transplant-related vascular disease. In some embodiments, the ADH inhibitor, AKR inhibitor, and/or SNO-CoAR inhibitor is useful in reducing the risk of recurrent cardiovascular events.

As will be appreciated by one of skill in the art, diseases or disorders that are generally addressable (either treatable or preventable) through the use of statins can also benefit from the application of the ADH inhibitor, AKR inhibitor, and/or SNO-CoAR inhibitor. In addition, in some embodiments, disorders or disease that can benefit from the prevention of cholesterol synthesis or increased LDLR expression can also be treated by various embodiments of the ADH inhibitor, AKR inhibitor, and/or SNO-CoAR inhibitor. In addition, as will be appreciated by one of skill in the art, the use of the ADH inhibitor, AKR inhibitor, and/or SNO-CoAR inhibitor can be especially useful in the treatment of diabetes. Not only is diabetes a risk factor for coronary heart disease, but insulin increases the expression of PCSK9. That is, people with Diabetes have elevated plasma lipid levels (which can be related to high PCSK9 levels) and can benefit from lowering those levels. This is generally discussed in more detail in Costet et al. ("Hepatic PCSK9 Expression is Regulated by Nutritional Status via Insulin and Sterol Regulatory Element-binding Protein 1C", J. Biol. Chem., 281: 6211-6218, 2006), the entirety of which is incorporated herein by reference.

In some embodiments, the ADH inhibitor, AKR inhibitor, and/or SNO-CoAR inhibitor is administered to those who have diabetes mellitus, abdominal aortic aneurysm, atherosclerosis and/or peripheral vascular disease in order to decrease their serum cholesterol levels to a safer range. In some embodiments, the ADH inhibitor, AKR inhibitor, and/or SNO-CoAR inhibitor is administered to patients at risk of developing any of the herein described disorders. In some embodiments, the ADH inhibitor, AKR inhibitor, and/or SNO-CoAR inhibitor is administered to subjects that smoke, or used to smoke (i.e., former smokers), have hypertension or a familial history of early heart attacks.

In some embodiments, the AKR inhibitor administered to a subject can be a partially selective AKR1A1 inhibitor and/or partially selective AKR1B1 inhibitor. For example, the AKR inhibitor can inhibit both AKR1A1 and AKR1B1, inhibit AKR1B1 at a lower $IC_{50}$ than AKR1A1, or inhibit AKR1A1 at a lower $IC_{50}$ than AKR1B1. Optionally, a selective or partially selective AKR1A1 inhibitor can be administered in combination with a selective or partially selective AKR1B1 inhibitor.

In some embodiments, the AKR1A1 inhibitor can have an $IC_{50} \leq 5$ μM, $\leq 1$ μM, or $\leq 100$ nM. In other embodiments, the AKR1A1 inhibitor can have a selectivity for AKR1A1 versus AKR1B1 $\geq 2$ times, $\geq 5$ times, $\geq 10$ times, $\geq 20$ times, $\geq 30$ times, $\geq 40$ times, $\geq 50$ times or more times. In other embodiments, the AKR1A1 inhibitor can have a selectivity for AKR1A1 versus other AKRs $\geq 2$ times, $\geq 5$ times, $\geq 10$ times, $\geq 20$ times, $\geq 30$ times, $\geq 40$ times, $\geq 50$ times or more times. In still other embodiments, the AKR1A1 inhibitor can have an AKR1A1 $IC_{50} \leq 400$ nM, $\leq 300$ nM, $\leq 200$ nM, $\leq 100$ nM, $\leq 50$ nM, or $\leq 25$ nM and a combined AKR1B1 and AKR1A1 $IC_{50} \leq 500$ nM, $\leq 400$ nM, $\leq 300$ nM, $\leq 200$ nM (e.g., less than 100 nM).

In some embodiments, the selectivity of the AKR inhibitor for AKR1A1 inhibition versus other AKRs, such as AKR1B1, can be measured using S-nitroso-Coenzyme A (SNO-CoA) as a substrate. In this instance where SNO-CoA is used as a substrate to measure AKR activity, the AKR inhibitor can have a selectivity for AKR1A1 versus AKR1B1 of $\geq 2$ times, $\geq 5$ times, $\geq 10$ times, $\geq 20$ times, $\geq 30$ times, $\geq 40$ times, $\geq 50$ times or more. In some embodiments, the AKR inhibitor can have neglible inhibition of AKR1B1 activity of SNO-CoA, and particularly compared to AKR1A1 activity.

In other embodiments, the AKR1B1 inhibitor can have an $IC_{50} \leq 5$ μM, $\leq 1$ μM, or $\leq 100$ nM. In other embodiments, the AKR1B1 inhibitor can have a selectivity for AKR1B1 versus AKR1A1 $\geq 2$ times, $\geq 5$ times, $\geq 10$ times, $\geq 20$ times, $\geq 30$ times, $\geq 40$ times, $\geq 50$ times or more times. In other embodiments, the AKR1B1 inhibitor can have a selectivity for AKR1B1 versus other AKRs $\geq 50$ times. In still other embodiments, the AKR1B1 inhibitor can have an AKR1B1 $IC_{50} \leq 300$ nM, $\leq 200$ nM, $\leq 100$ nM, $\leq 50$ nM, or $\leq 25$ nM and a combined AKR1B1 and AKR1A1 $IC_{50} \leq 500$ nM, $\leq 400$ nM, $\leq 300$ nM, $\leq 200$ nM (e.g., less than 100 nM).

Examples of selective and partially selective AKR1A1 inhibitors, including partially selective inhibitors of AKR1A1 activity of SNO-CoA, can include Imirestat (2,7-Difluoro-2'H,5'H-spiro[fluorene-9,4'-imidazolidine]-2',5'-dione) and analogues thereof. Other examples of selective and partially selective AKR1A1 inhibitors can include Tolrestat, Oxo-Tolrestat, Epalrestat, Fidarestat, Statil, Sorbinil, Ranirestat, and Minalrestat.

In some embodiments, the imirestat analogues can include compounds selected from the group consisting of:

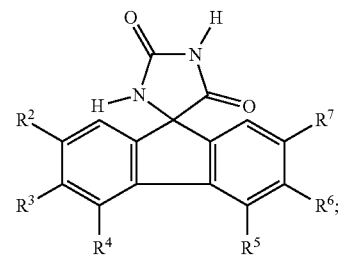

-continued
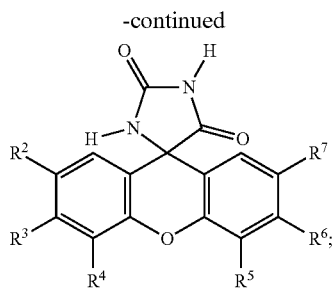
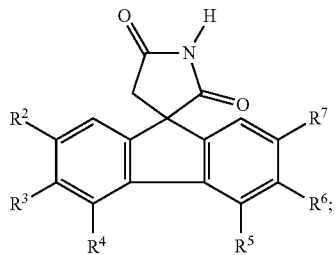
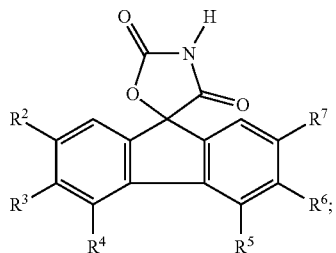
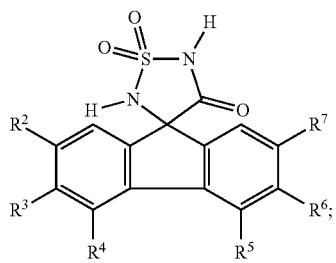
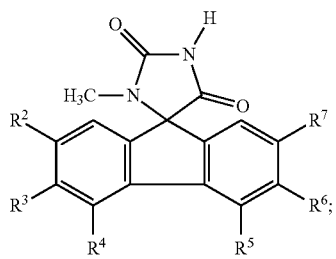
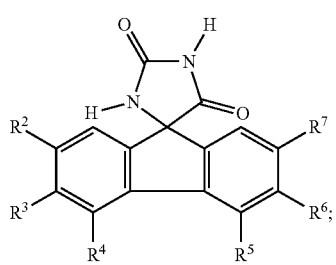
-continued
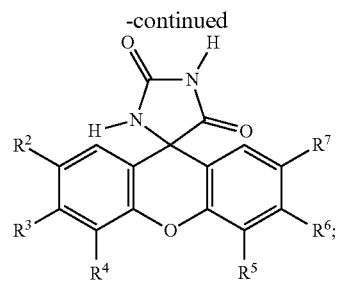
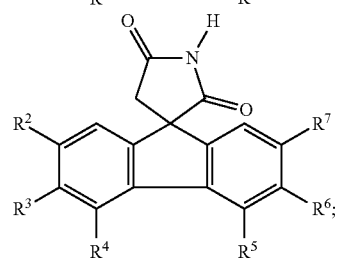
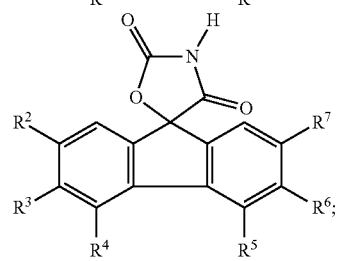
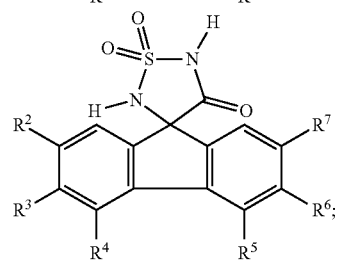
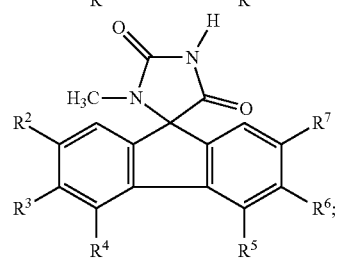
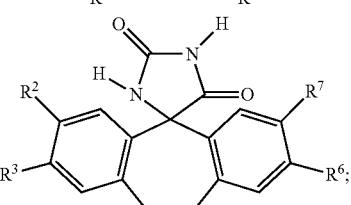
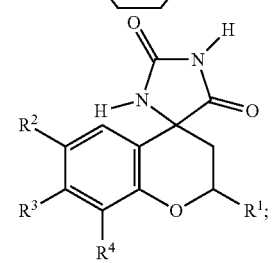

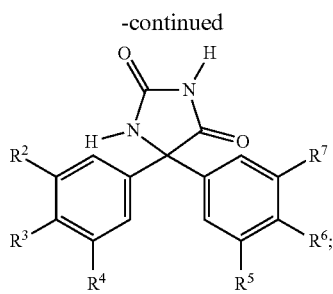

each, $R^1$, $R^2$, $R^3$, $R^4$, $R^5$, $R^6$, and $R^7$ are the same or different and are one or more substituent selected from the group consisting of hydrogen, halogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), carbamido (—NH—(CO)—NH$_2$), cyano(—CN), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO$_2$NR2 where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N (aryl), where R=hydrogen, alkyl, aryl, alkaryl, etc.), sulfo (—SO$_2$—OH), sulfonato (—SO$_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide, and combinations thereof; and pharmaceutically acceptable salts thereof.

In other embodiments, the imirestat analogues can include compounds selected from the group consisting of:

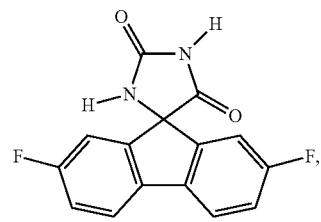

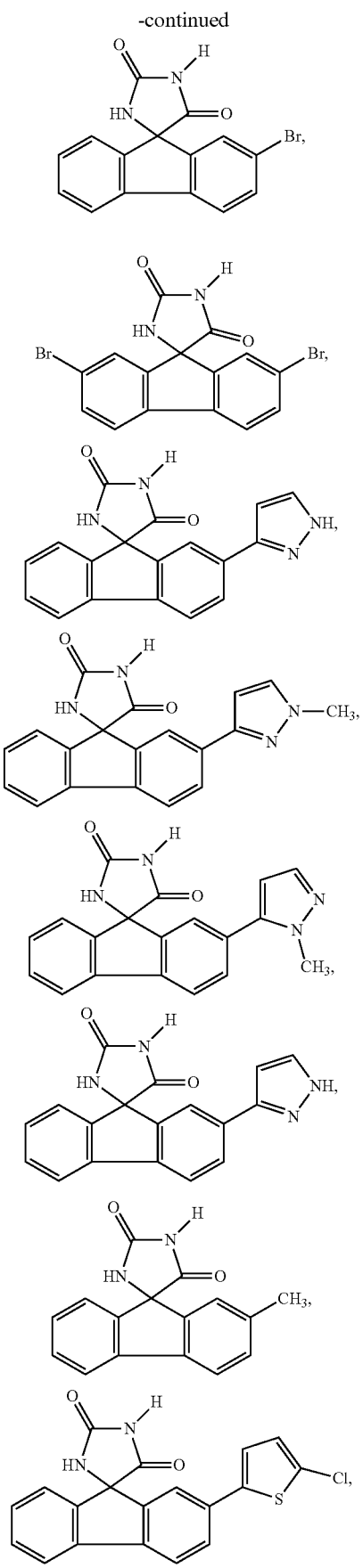

-continued
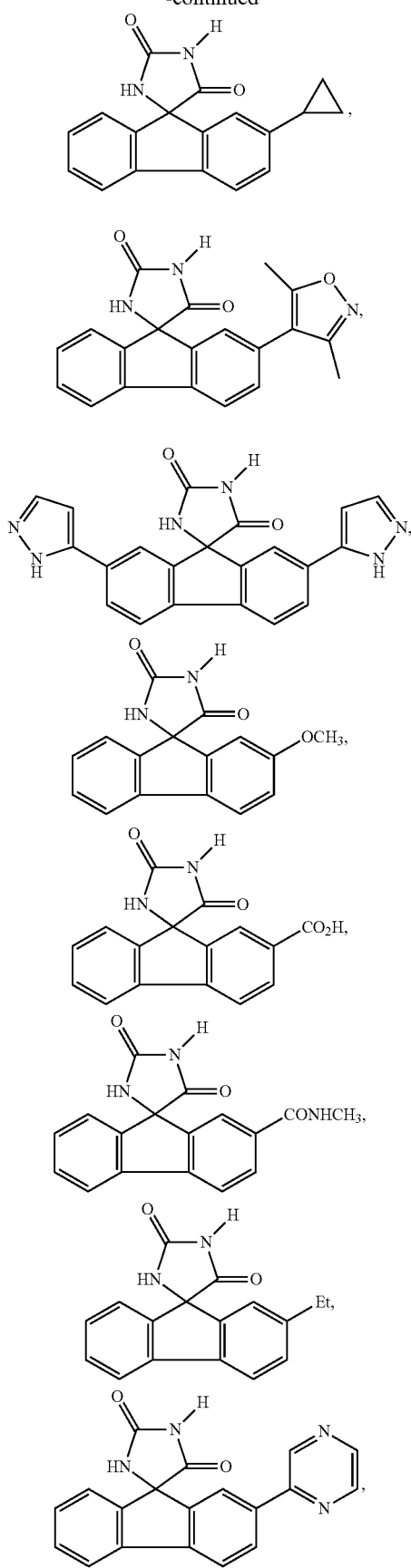
-continued
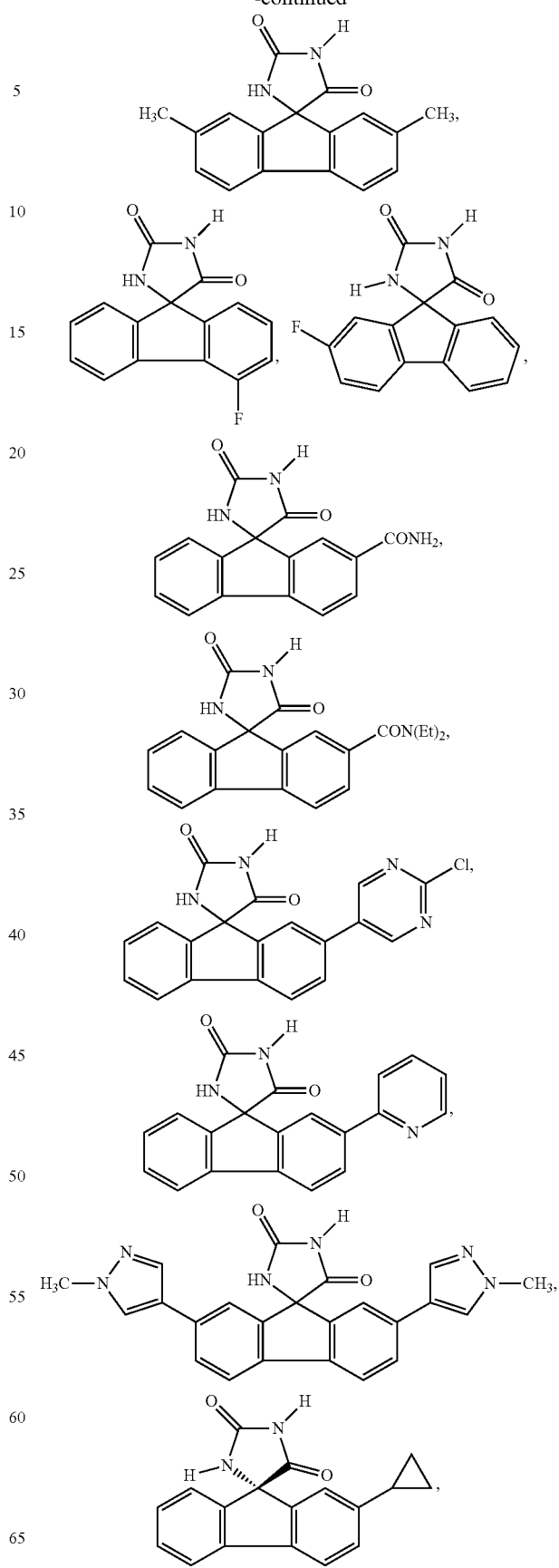

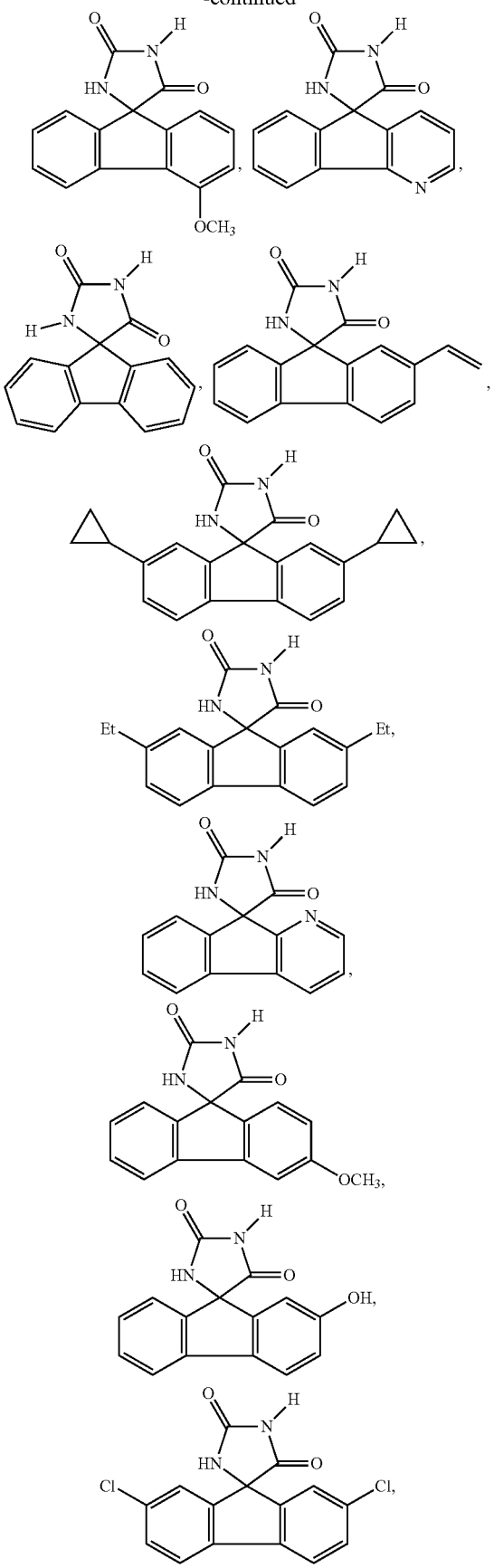
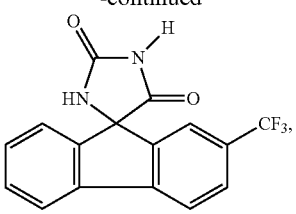
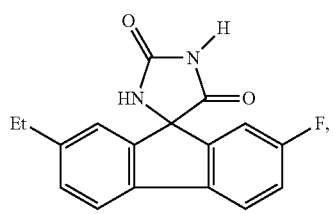
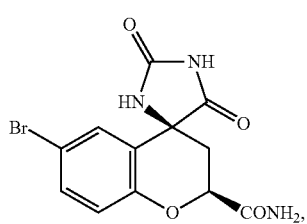
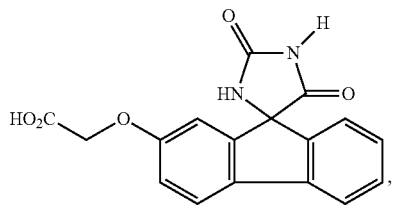
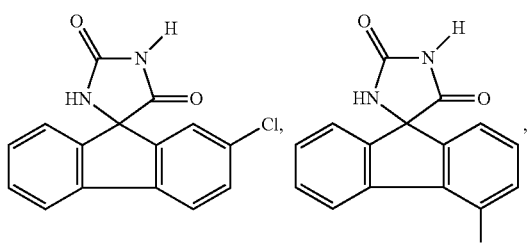
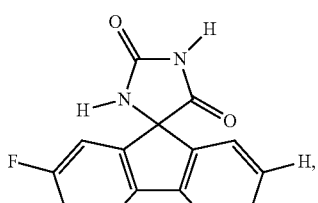
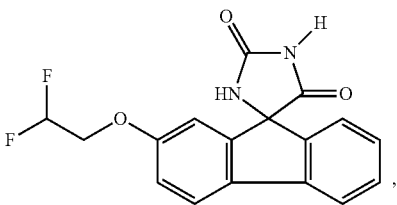

-continued
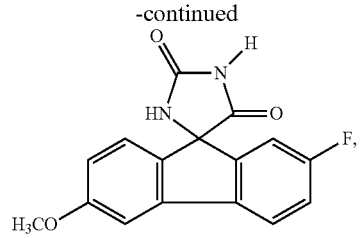
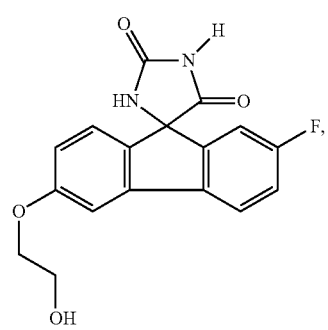
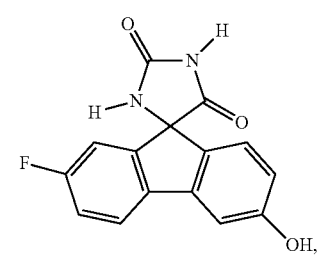
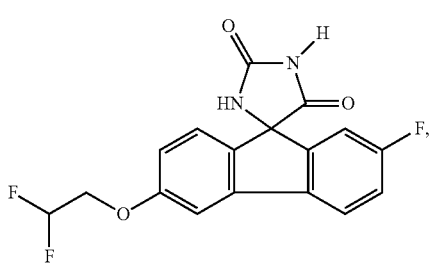
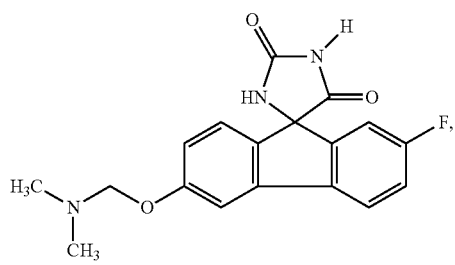
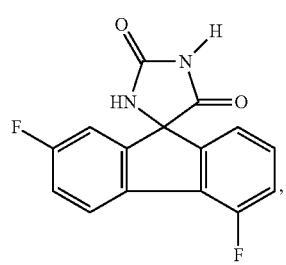
-continued
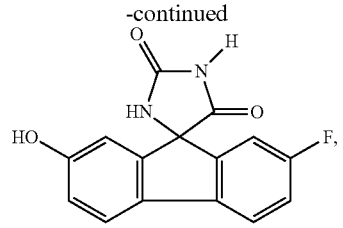
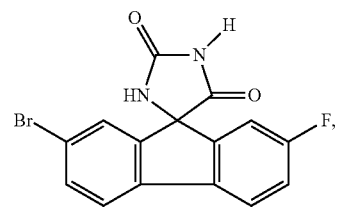
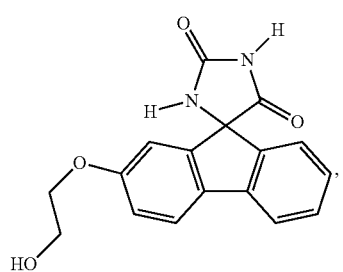
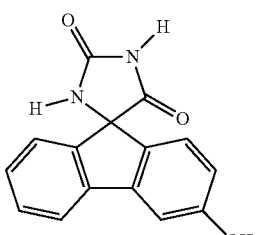
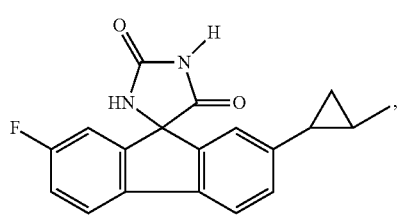
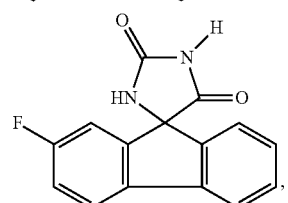
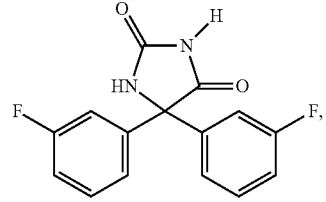

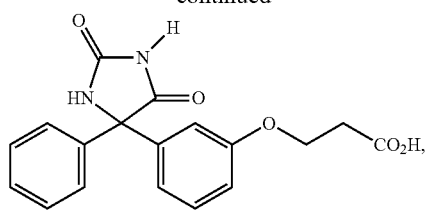
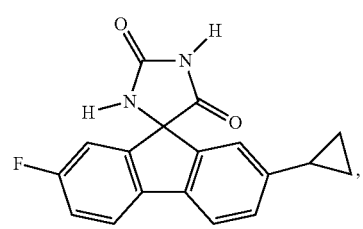
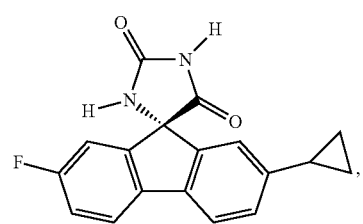
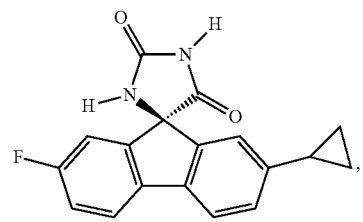
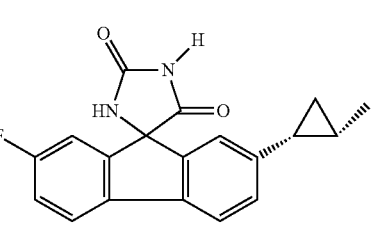
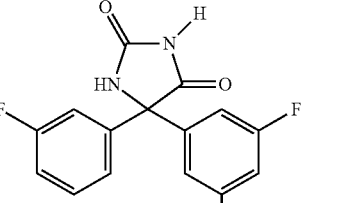
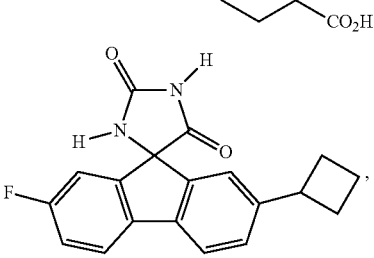
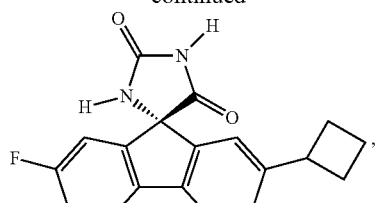
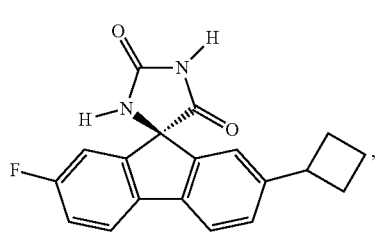
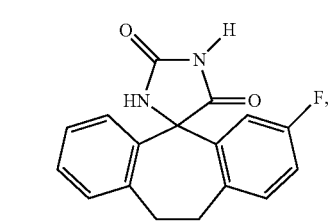
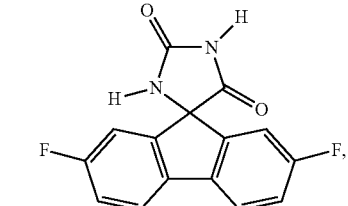
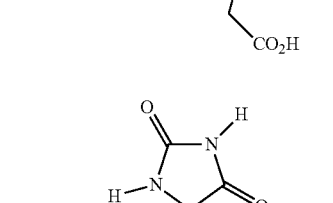
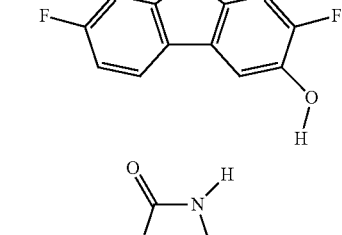
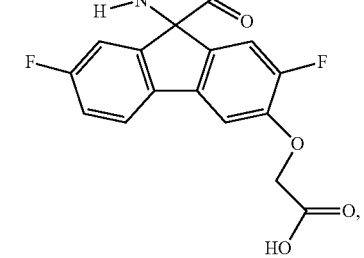

-continued
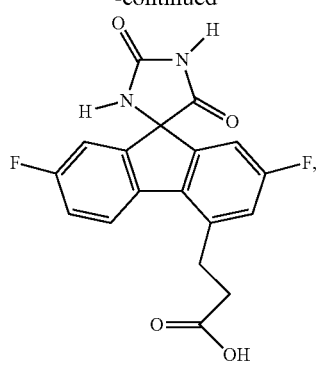
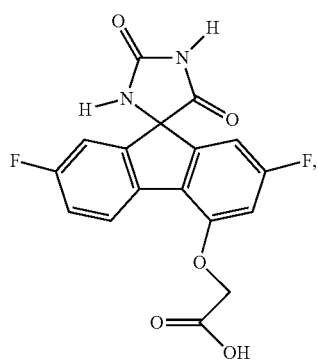
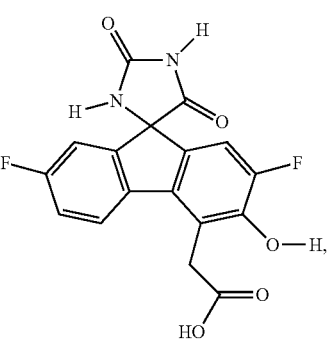
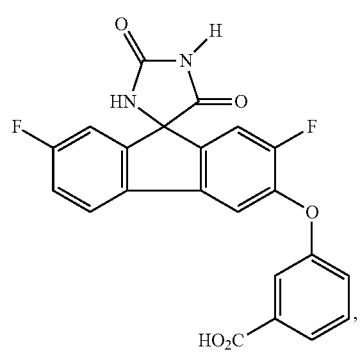
-continued
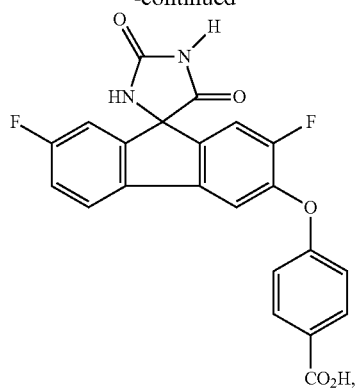
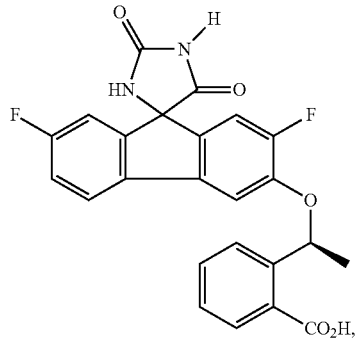
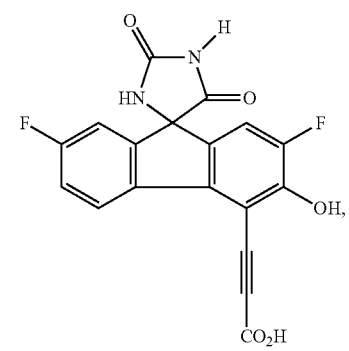
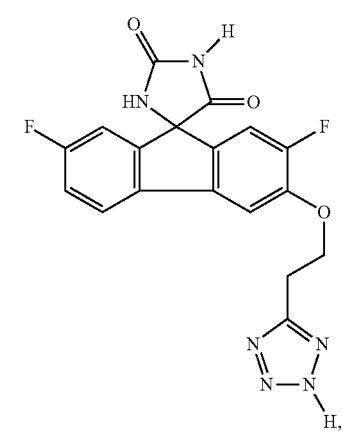

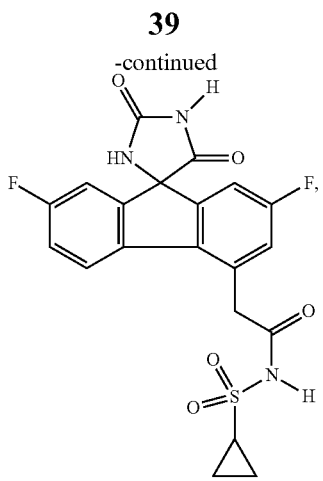
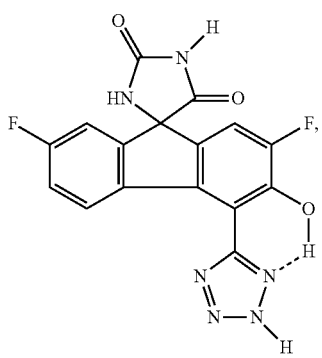
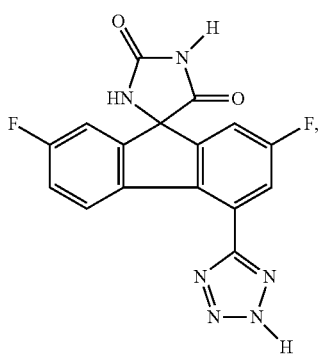
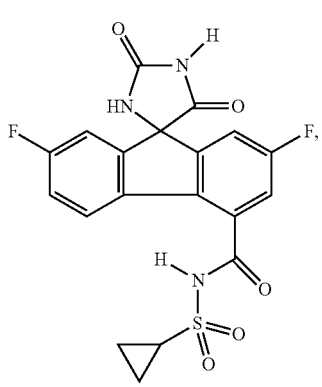
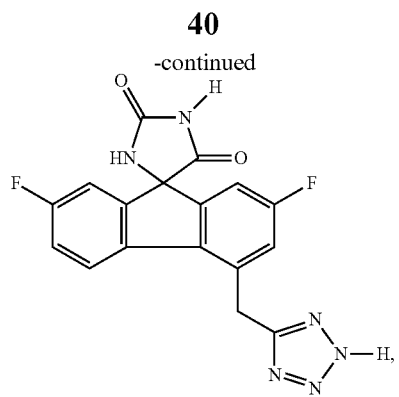
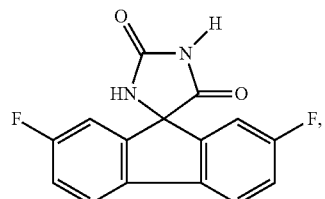
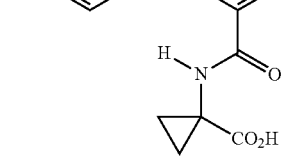
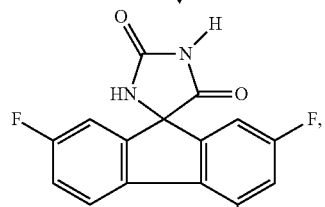
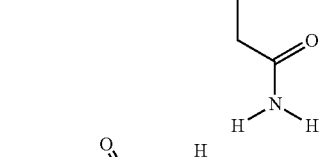
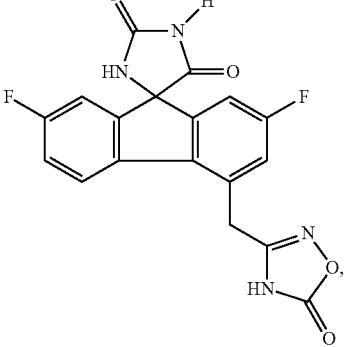

and pharmaceutically acceptable salts thereof.

Still other examples of selective and/or partially selective AKR1A1 inhibitor are disclosed in the following publications: Mechanism of Human Aldehyde Reductase: Characterization of the Active Site Pocket, Oleg A. Barski et al., Biochemistry 1995,34, 11264-11275, In vivo role of aldehyde reductase, M. Takahashi et al., Biochim Biophys Acta. 2012 November; 1820(11):1787-96, The Aldo-Keto Reductase Superfamily and its Role in Drug Metabolism and Detoxification, Oleg A. Barski et al., Drug Metab Rev. 2008; 40(4): 553-624, Asborin Inhibits Aldo/Keto Reductase 1A1, Matthias Scholz et al., Chem Med Chem, 2011, 6, 89-93, Inhibition of Aldehyde Reductase by Aldose Reductase Inhibitors, Sanai Sato et al., Biochemical Pharmacology, 1990. 40, 1033-1042, Inhibition of human aldose and aldehyde reductases by non-steroidal anti-inflammatory drugs, D. Michelle Ratliff et al., Advances in Experimental Medicine and Biology, Volume: 463, Issue: Enzymology and Molecular Biology of Carbonyl Metabolism 7, Pages: 493-499 (1999.), Inhibition of aldehyde reductases, Philip J. Schofield et al., Progress in Clinical and Biological Research, 1987, 232, Issue: Enzymol. Mol. Biol. Carbonyl Metab., 287-96, Aldose Reductase Inhibitors as Potential Therapeutic Drugs of Diabetic Complications, By Changjin Zhu, DOI: 10.5772/54642, Aldose Reductase Inhibitors: A Potential New Class of Agents for the Pharmacological Control of Certain Diabetic Complications, Peter F. Kador et al., Journal of Medicinal Chemistry, 1985, 28, 841-849, Recent clinical experience with aldose reductase inhibitors, H. M. J. Krans, Journal of Diabetes and its Complications, 1992, 6, 39-44, A Novel Series of Non-Carboxylic Acid, Non-Hydantoin Inhibitors of Aldose Reductase with Potent Oral Activity in Diabetic Rat Models: 6-(5-Chloro-3-methylbenzofuran-2-sulfonyl)-2H-pyridazin-3-one and Congeners, Banavara L. Mylari et al., J. Med. Chem. 2005, 48, 6326-6339, A Diverse Series of Substituted Benzenesulfonamides as Aldose Reductase Inhibitors with Antioxidant Activity: Design, Synthesis, and in Vitro Activity, Polyxeni Alexiou et al., J. Med. Chem. 2010, 53, 7756-7766, Aldose Reductase Inhibitors as Potential Therapeutic Drugs of Diabetic Complications, By Changjin Zhu, DOI: 10.5772/54642, Aldose Reductase Inhibitors: A Potential New Class of Agents for the Pharmacological Control of Certain Diabetic Complications, Peter F. Kador et al., Journal of Medicinal Chemistry, 1985, 28, 841-849, Recent clinical experience with aldose reductase inhibitors, H. M. J. Krans, Journal of Diabetes and its Complications, 1992, 6, 39-44, A Novel Series of Non-Carboxylic Acid, Non-Hydantoin Inhibitors of Aldose Reductase with Potent Oral Activity in Diabetic Rat Models: 6-(5-Chloro-3-methylbenzofuran-2-sulfonyl)-2H-pyridazin-3-one and Congeners, Banavara L. Mylari et al., J. Med. Chem. 2005, 48, 6326-6339, A Diverse Series of Substituted Benzenesulfonamides as Aldose Reductase Inhibitors with Antioxidant Activity: Design, Synthesis, and in Vitro Activity, Polyxeni Alexiou et al., J. Med. Chem. 2010, 53, 7756-7766, all of which are incorporated herein by reference in their entirety. It will be appreciated that any potential selective or partially selective AKR1A1 inhibitors can be used in the compositions and methods recited herein.

The ADH inhibitor can be include auramine O, allicin, 1,5-anilinonaphthalenesulfonic acid, 1,7-anilinonaphthalenesulfonic acid, 1,8-anilinonaphthalenesulfonic acid, berberine, canavanine, 2,2'-diprypyl, imidazole, m-methylbenzamide, 4-methylpyrazole, pyrazole, 4-pentylpyrazole, O-phenanthroline, alrestatin, anthranic acid, O-carboxybenzaldehyde, 2,3-dimethylsuccinic acid, ethacrynic acid, isonicotinic acid, phenacemide, quercetin, quercitrin, sorbinil, tetramethyleneglutaric acid, valproic acid, propranolol, 2,2,2-trichloroethanol, 4,5-diaminopyrazole and its derivatives and 2-ethyl-5-methyl-2H-3,4-diaminopyrazole. See U.S. Patent Application Publication 20030138390, which is incorporated herein by reference in its entirety.

Fomepizole (4-methylpyrazole) is also a competitive inhibitor of ADH. Pyrazole and its 4-substituted derivatives competitively inhibit the binding of alcohol substrates through the formation of a tight enzyme.NAD$^+$.inhibitor complex, in which pyrazole nitrogens interact with both zinc and NAD$^+$. Xie et al., J. Biol. Chem., 272:18558-18563 (1997), herein incorporated by reference.

CNAD (5-beta-D-ribofuranosylnicotinamide adenine dinucleotide) is an isomeric and isomeric analogue of NAD, in which the nicotinamide ring is linked to the sugar via a C-glycosyl (C5-C1') bond. CNAD acts as a general dehydrogenase inhibitor but shows unusual specificity and affinity for liver alcohol dehydrogenase. Goldstein et al., J. Med. Chem., 37:392-9 (1994), herein incorporated by reference.

Other ADH inhibitors include dimethyl sulfoxide, Perlman and Wolff, Science, 160:317-9 (1968); and p-methylbenzyl hydroperoxide, Skursky et al., Biochem Int., 26:899-904 (1992), herein incorporated by reference.

In some embodiments, the ADH inhibitor can be a selective ADH6 inhibitor or partially selective ADH6 inhibitor that does not inhibit ADH3. In other embodiments, the ADH inhibitor does not inhibit ADH3 but inhibits other ADHs, such as ADH6.

In other embodiments, the ADH inhibitor and/or AKR inhibitor can include an agent that reduces or inhibits ADH and/or AKR expression, such as ADH6 expression or AKR1A1 expression, in tissue or cells of a subject in need thereof. "Expression", means the overall flow of information from a gene to produce a gene product (typically a protein, optionally post-translationally modified or a functional/structural RNA).

In some embodiments, the agent can include an RNAi construct that inhibits or reduces expression of the ADH and/or AKR expression in a cell. RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner.

As used herein, the term "dsRNA" refers to siRNA molecules or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

As used herein, the term "RNAi construct" is a generic term used throughout the specification to include small interfering RNAs (siRNAs), hairpin RNAs, and other RNA species, which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences.

The choice of promoter and other regulatory elements generally varies according to the intended host cell. In general, expression vectors of utility in recombinant DNA techniques are often in the form of "plasmids" which refer to circular double stranded DNA loops, which, in their vector form are not bound to the chromosome. In the present specification, "plasmid" and "vector" are used interchangeably as the plasmid is the most commonly used form of vector. However, the application describes other forms of expression vectors that serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, embodiments tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, a modified ribonucleotide can be introduced by in vitro enzymatic or organic synthesis.

Methods of chemically modifying RNA molecules can be adapted for modifying RNAi constructs (see for example, *Nucleic Acids Res*, 25:776-780; *J Mol Recog* 7:89-98; *Nucleic Acids Res* 23:2661-2668; *Antisense Nucleic Acid Drug Dev* 7:55-61). Merely to illustrate, the backbone of an RNAi construct can be modified with phosphorothioates, phosphoramidate, phosphodithioates, chimeric methylphosphonate-phosphodie-sters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount, which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules described herein can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (*Proc Natl Acad Sci USA*, 98:9742-9747; *EMBO J*, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the Drosophila in vitro system is used. In this embodiment, dsRNA is combined with a soluble extract derived from Drosophila embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, *Genes Dev*, 2002, 16:948-58; *Nature*, 2002, 418:38-9; *RNA*, 2002, 8:842-50; and *Proc Nail Acad Sci*, 2002, 99:6047-52. Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an example of a vector for bi-directional transcription of a transgene to yield both sense and antisense RNA transcripts of the same transgene in a eukaryotic cell. Accordingly, certain embodiments provide a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

In some embodiments, a lentiviral vector can be used for the long-term expression of a siRNA, such as a short-hairpin RNA (shRNA), to knockdown expression of the RPTP in a cancer cell. Although there have been some safety concerns about the use of lentiviral vectors for gene therapy, self-inactivating lentiviral vectors are considered good candidates for gene therapy as they readily transfect mammalian cells.

By way of example, short-hairpin RNA (shRNA) down regulation of the AKR1A1 expression can be created using OligoEngene software (OligoEngine, Seattle, Wash.) to identify sequences as targets of siRNA. The oligo sequences can be annealed and ligated into linearized pSUPER RNAi vector (OligoEngine, Seattle, Wash.) and transformed in *E coli* strain DH5a cells. After positive clones are selected, plasmid can be transfected into 293T cells by calcium precipitation. The viral supernatant collected containing shRNA can then be used to infect mammalian cells in order to down regulate the AKR1A1.

AKR1A1 siRNA, shRNA plasmids, and shRNA lentiviral particle gene silencers are commercially available from Santa Cruz Biotechnology under the product names sc-78566, sc-78566-SH, and sc-78566-V.

In another embodiment, the ADH and/or AKR inhibitor can include antisense oligonucleotides. Antisense oligonucleotides are relatively short nucleic acids that are complementary (or antisense) to the coding strand (sense strand) of the mRNA encoding a particular protein. Although antisense oligonucleotides are typically RNA based, they can also be DNA based. Additionally, antisense oligonucleotides are often modified to increase their stability.

The binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding a specific protein. Accordingly, antisense oligonucleotides decrease the expression and/or activity of a particular protein (e.g., AKR1A1).

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups, such as peptides (e.g., for targeting host cell receptors), or agents facilitating transport across the cell membrane (see, e.g., *Proc Natl Acad Sci* 86:6553-6556; *Proc Natl Acad Sci* 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents (See, e.g., *BioTechniques* 6:958-976) or intercalating agents. (See, e.g., *Pharm Res* 5:539-549). To this end, the oligonucleotide may be conjugated or coupled to another molecule.

Oligonucleotides described herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209), methylphosphonate oligonucleotides can be prepared by use of controlled pore glass polymer supports (*Proc Natl Acad Sci* 85:7448-7451).

The selection of an appropriate oligonucleotide can be performed by one of skill in the art. Given the nucleic acid sequence encoding a particular protein, one of skill in the art can design antisense oligonucleotides that bind to that protein, and test these oligonucleotides in an in vitro or in vivo system to confirm that they bind to and mediate the degradation of the mRNA encoding the particular protein. To design an antisense oligonucleotide that specifically binds to and mediates the degradation of a particular protein, it is important that the sequence recognized by the oligonucleotide is unique or substantially unique to that particular protein. For example, sequences that are frequently repeated across protein may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for a particular protein.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense oligonucleotide sufficient to suppress translation on endogenous mRNAs in certain instances. Therefore, another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Expression of the sequence encoding the antisense RNA can be by a promoter known in the art to act in mammalian, preferably human cells. Such promoters can be inducible or constitutive. Such promoters include but are not limited to: the SV40 early promoter region (*Nature* 290:304-310), the promoter contained in the 3' long terminal repeat of Rous sarcoma virus (*Cell* 22:787-797), the herpes thymidine kinase promoter (*Proc Natl Acad Sci* 78:1441-1445), the regulatory sequences of the metallothionein gene (*Nature* 296:39-42), etc. A type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

The ADH inhibitors, AKR inhibitors, and/or SNO-CoAR inhibitors can be provided in pharmaceutical compositions with at least one pharmaceutically acceptable carrier. Suitable carriers are described in "Remington: The Science and Practice, Twentieth Edition," published by Lippincott Williams & Wilkins, which is incorporated herein by reference. Pharmaceutical compositions according to the invention may also comprise one or more non-inventive compound active agents.

The compositions comprising ADH inhibitors, AKR inhibitors, and/or SNO-CoAR inhibitors can be utilized in any pharmaceutically acceptable dosage form, including, but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the ADH inhibitors, AKR inhibitors, and/or SNO-CoAR inhibitors can be formulated: (a) for administration selected from the group consisting of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from the group consisting of liquid dispersions, gels, aerosols, ointments, creams, tablets, sachets, and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

For respiratory disorders, an inhalation formulation can be used to achieve high local concentrations. Formulations suitable for inhalation include dry power or aerosolized or vaporized solutions, dispersions, or suspensions capable of being dispensed by an inhaler or nebulizer into the endobronchial or nasal cavity of infected patients to treat upper and lower respiratory bacterial infections.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol, or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates, or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes, or multiple dose vials made of glass or plastic.

Pharmaceutical compositions suitable for injectable use may comprise sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.), or phosphate buffered saline (PBS). In all cases, the composition must be sterile and should be fluid to the extent that easy syringability exists. The pharmaceutical composition should be stable under the conditions of manufacture and storage and should be preserved against the contaminating action of microorganisms such as bacteria and fungi.

The carrier can be a solvent or dispersion medium comprising, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent in the required amount in an appropriate solvent with one or a combination of ingredients enumerated above, as required, followed by filtered sterilization. Generally, dispersions are prepared by incorporating at least one compound of the invention into a sterile vehicle that contains a basic dispersion medium and any other required ingredients. In the case of sterile powders for the preparation of sterile injectable solutions, exemplary methods of preparation include vacuum drying and freeze-drying, both of which yield a powder of a compound of the invention plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the compound of the invention can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from pressured container or dispenser that contains a suitable propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, the ADH inhibitors, AKR inhibitors, and/or SNO-CoAR inhibitors are prepared with carriers that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the compounds of the invention may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of the compound of the invention calculated to produce the desired therapeutic effect in association with the required pharmaceutical carrier. The specification for the dosage unit forms of the invention are dictated by and directly dependent on the unique characteristics of the compound of the invention and the particular therapeutic effect to be achieved, and the limitations inherent in the art of compounding such an active agent for the treatment of individuals.

Pharmaceutical compositions that include the ADH inhibitors, AKR inhibitors, and/or SNO-CoAR inhibitors can comprise one or more pharmaceutical excipients. Examples of such excipients include, but are not limited to binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, silicified microcrystalline cellulose, gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, cross-povidone, sodium starch glycolate, and mixtures thereof; (4) lubricants, including agents that act on the flowability of a powder to be compressed, include magnesium stearate, colloidal silicon dioxide, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose; lactose such as lactose monohydrate, and lactose anhydrous; dibasic calcium phosphate, mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

In some embodiments, the ADH inhibitors, AKR inhibitors, and/or SNO-CoAR inhibitors including pharmaceutical compositions comprising the ADH inhibitors, AKR inhibitors, and/or SNO-CoAR inhibitors can be used in methods for preventing or treating (e.g., alleviating one or more symptoms of) medical conditions. The methods comprise administering a therapeutically effective amount of the ADH inhibitors, AKR inhibitors, and/or SNO-CoAR inhibitors to a patient or subject in need thereof. The compositions can also be used for prophylactic therapy.

The patient can be any animal, domestic, livestock, or wild, including, but not limited to cats, dogs, horses, pigs, and cattle, and preferably human patients. As used herein, the terms patient and subject may be used interchangeably.

In general, the dosage, i.e., the therapeutically effective amount, ranges from 1 µg/kg to 10 g/kg and often ranges from 10 µg/kg to 1 g/kg or 10 µg/kg to 100 mg/kg body weight of the subject being treated, per day.

In certain embodiments, one or more pharmaceutical compositions of the the ADH inhibitors, AKR inhibitors, and/or SNO-CoAR inhibitors can be co-administered with one or more other pharmaceutical agents. In certain embodiments, such one or more other pharmaceutical agents are designed to treat the same disease or condition as the one or more pharmaceutical compositions of the present invention. In certain embodiments, such one or more other pharmaceutical agents are designed to treat a different disease or condition as the one or more pharmaceutical compositions of the present invention. In certain embodiments, such one or more other pharmaceutical agents are designed to treat an undesired effect of one or more pharmaceutical compositions described herein. In certain embodiments, one or more pharmaceutical compositions of described herein are co-administered with another pharmaceutical agent to treat an undesired effect of that other pharmaceutical agent. In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately. For example, a composition may comprise a pharmaceutical agent for separate, sequential, or simultaneous administration with an antisense compound.

In certain embodiments, pharmaceutical agents that may be co-administered with a pharmaceutical composition described herein include lipid-lowering agents. In certain such embodiments, pharmaceutical agents that may be co-administered with a pharmaceutical composition of the present invention include, but are not limited to atorvastatin, simvastatin, rosuvastatin, and ezetimibe. In certain such embodiments, the lipid-lowering agent is administered prior to administration of a pharmaceutical composition described herein. In certain such embodiments, the lipid-lowering agent is administered following administration of a pharmaceutical composition described herein. In certain such embodiments the lipid-lowering agent is administered at the same time as a pharmaceutical composition described herein. In certain such embodiments the dose of a co-administered lipid-lowering agent is the same as the dose that would be administered if the lipid-lowering agent was administered alone. In certain such embodiments the dose of a co-administered lipid-lowering agent is lower than the dose that would be administered if the lipid-lowering agent was administered alone. In certain such embodiments the dose of a co-administered lipid-lowering agent is greater than the dose that would be administered if the lipid-lowering agent was administered alone.

In certain embodiments, a co-administered lipid-lowering agent is a HMG-CoA reductase inhibitor. In certain such embodiments the HMG-CoA reductase inhibitor is a statin. In certain such embodiments, the statin is selected from, for example, atorvastatin, simvastatin, pravastatin, fluvastatin, and rosuvastatin.

In certain embodiments, a co-administered lipid-lowering agent is a cholesterol absorption inhibitor. In certain such embodiments, cholesterol absorption inhibitor is ezetimibe.

In certain embodiments, a co-administered lipid-lowering agent is a co-formulated HMG-CoA reductase inhibitor and cholesterol absorption inhibitor. In certain such embodiments the co-formulated lipid-lowering agent is ezetimibe/simvastatin.

In certain embodiments, a co-administered lipid-lowering agent is a microsomal triglyceride transfer protein inhibitor (MTP inhibitor).

In certain embodiments, a co-administered lipid-lowering agent is an oligonucleotide targeted to ApoB.

In certain embodiments, a co-administered pharmaceutical agent is a bile acid sequestrant. In certain such embodiments, the bile acid sequestrant is selected from cholestyramine, colestipol, and colesevelam.

In certain embodiments, a co-administered pharmaceutical agent is a nicotinic acid. In certain such embodiments, the nicotinic acid is selected from immediate release nicotinic acid, extended release nicotinic acid, and sustained release nicotinic acid.

In certain embodiments, a co-administered pharmaceutical agent is a fibric acid. In certain such embodiments, a fibric acid is selected from gemfibrozil, fenofibrate, clofibrate, bezafibrate, and ciprofibrate.

Further examples of pharmaceutical agents that may be co-administered with a pharmaceutical compositions, which include the the ADH inhibitors, AKR inhibitors, and/or SNO-CoAR inhibitors described herein, include, but are not limited to, corticosteroids, including but not limited to prednisone; LXR agonists; immunoglobulins, including, but not limited to intravenous immunoglobulin (IVIg); analgesics (e.g., acetaminophen); anti-inflammatory agents, including, but not limited to non-steroidal anti-inflammatory drugs (e.g., ibuprofen, COX-1 inhibitors, and COX-2 inhibitors); salicylates; antibiotics; antivirals; antifungal agents; antidiabetic agents (e.g., biguanides, glucosidase inhibitors, insulins, sulfonylureas, and thiazolidenediones); adrenergic modifiers; diuretics; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

In certain embodiments, the pharmaceutical compositions of the present invention may be administered in conjunction with a lipid-lowering therapy. In certain such embodiments, a lipid-lowering therapy is therapeutic lifestyle change. In certain such embodiments, a lipid-lowering therapy is LDL apheresis.

In other embodiments, the ADH inhibitors, AKR inhibitors, and/or SNO-CoAR inhibitors can be used in combination with surgical procedures such as angioplasty for cardiovascular diseases. Angioplasty is often accompanied by the placement of a reinforcing a metallic tube shaped structure known as a "stent" into a damaged coronary artery. For more serious conditions, open heart surgery such as coronary bypass surgery may be required. These surgical procedures entail using invasive surgical devices and/or implants, and are associated with a high risk of restenosis and thrombosis. Accordingly, the ADH inhibitors, AKR inhibitors, and/or SNO-CoAR inhibitors may be used as coatings on surgical devices (e.g., catheters) and implants (e.g., stents) to reduce the risk of restenosis and thrombosis associated with invasive procedures used in the treatment of cardiovascular diseases.

EXAMPLE

Animals

AKR1A1$^{-/-}$ mice were generated by Deltagen, Inc. C57BL6/J and ApoE$^{-/-}$ mice were purchased from The Jackson Laboratory. CETP-ApoB100 transgenic mice were purchased from Taconic Biosciences. All mice were maintained under a 12-hour light/dark cycle. For imirestat treatment studies, mice were provided control chow or chow containing 0.0125% w/w imirestat (125 mg imirestat/1 kg chow) ad libitum. C57BL6/J and ApoE$^{-/-}$ mice were provided control chow or imirestat chow for 4 weeks starting at age 20 weeks; CETP-ApoB100 transgenic mice were provided control chow or imirestat chow for 8 weeks starting at age 10 weeks.

Blood Collection and Serum Separation

Prior to euthanasia, mice were fasted for the indicated length of time. Mice were euthanized under Isoflurane anesthesia via terminal exsanguination from the inferior vena cava and removal of vital organs. Collected blood was allowed to coagulate for 20 minutes at room temperature in a pediatric serum separator tube. Serum was separated by centrifugation at 2000 g for 20 minutes at 4° C. Serum was stored at −80° C. until analysis. For overnight fasted 12-week-old AKR1A1$^{-/-}$ mice (FIG. 5), whole blood was provided to University Hospitals' Clinical Laboratory (Cleveland, Ohio) for cholesterol analysis. Tissues were snap frozen in liquid nitrogen and stored at −80° C. until analysis.

Serum Analysis

Total serum cholesterol was determined by standard enzymatic assays. For lipoprotein cholesterol quantification, lipoprotein fractions were separated by gel filtration column chromatography. Approximately 70 fractions were collected and cholesterol in each fraction was quantified by standard enzymatic assays. Calibration of the column with purified lipoprotein fractions permitted quantification of cholesterol in various lipoprotein classes. Serum PCSK9 was quantified by solid phase sandwich ELISA.

AKR1A1 Activity Assays

The human AKR1A1 coding sequence was cloned into a pET21b bacterial expression vector. pET21b-AKR1A1 was transformed into Rosetta2(DE3)pLysS *E. coli* and expression was induced by the addition of 100 μM isopropyl-β-D-1-thiogalactopyranoside at $A_{600nm}$=0.4. Bacteria were grown for 4 hours at 25° C. and recombinant His-tagged SCoR was purified via Ni-affinity purification. Triplicate reactions were performed with 200 nM recombinant AKR1A1, 100 μM NADPH, 100 μM SNO-CoA, and increasing concentrations of imirestat dissolved in dimethyl sulfoxide (DMSO). SNO-CoA was prepared by reacting equal volumes of 0.1M CoA in 1M HCl and 0.1M NaNO$_2$ water containing 100 μM EDTA and 100 μM DTPA. Initial rates were calculated using absorbance decrease at 340 nm. IC$_{50}$ was calculated in GraphPad Prism 7 using non-linear regression analysis. For AKR1A1 liver activity following in-diet imirestat treatment, frozen liver tissue was dounce homogenized (30 dounces) in 50 mM phosphate buffer, pH 7.0 supplemented with 100 μM ethylenediaminetetraacetic acid (EDTA) and diethylenetriamine pentaacetate (DTPA) and 150 mM sodium chloride. Tissue lysate was clarified by centrifugation at 20000 g for 45 minutes, 4° C. Clarified supernatant was collected and the centrifugation was repeated. Assays for specific activity in liver lysates were performed in 50 mM phosphate buffer, pH 7.0 containing 100 μM SNO-CoA, 100 μM NADPH, 100 μM EDTA, and 100 μM DPTA. Reactions were initiated by the addition of liver lysate and specific activity was calculated from the change in absorbance at 340 nm, protein concentration, and an extinction coefficient of 7.06 mM$^{-1}$·cm$^{-1}$ (combined for SNO-CoA and NADPH).

FIG. 1 illustrates a graph showing total serum cholesterol levels in AKR1A1 deficient 12-week old mice compared to 12-week old wild-type mice. AKR1A1 deficient 12-week old male mice had reduced total serum cholesterol compared to 12-week old wild type mice.

Figure 2:
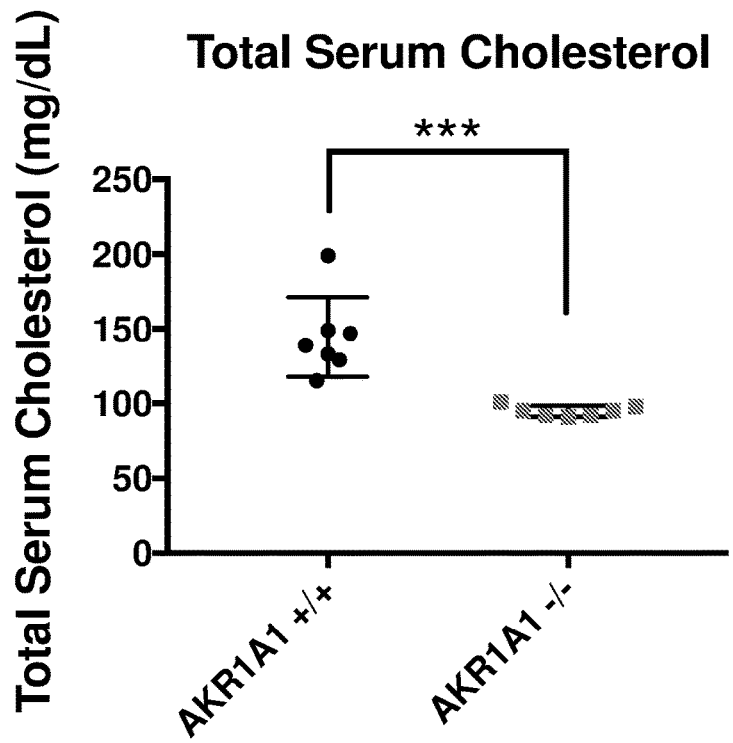
FIG. 2 illustrates a graph showing total serum cholesterol levels in AKR1A1 deficient 24-week mice compared to 24-week wild-type mice.

FIG. 2 illustrates a graph showing total serum cholesterol levels in AKR1A1 deficient 24-week old mice compared to 24-week old wild-type mice. AKR1A1 deficient 24-week old male mice had reduced total serum cholesterol compared to 24-week old wild type mice.

Figure 3:
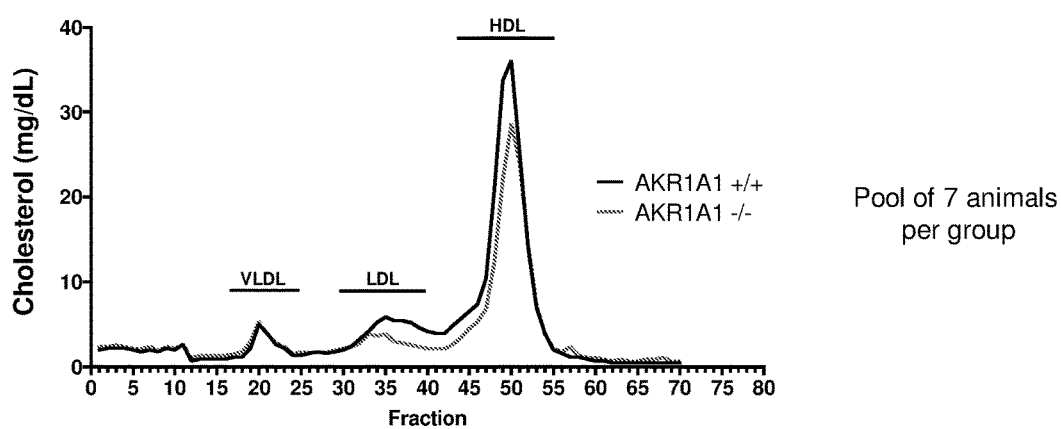
FIG. 3 illustrates a plot showing cholesterol fractionation in AKR1A1 deficient mice.

FIG. 3 illustrates plots showing cholesterol fractionation in AKR1A1 deficient 24-week old male mice and 24-week old wild type mice. The cholesterol fractionation confirmed reduced total serum cholesterol in AKR1A1 deficient 24-week old male mice compared to 24-week old wild type mice.

Figure 4:
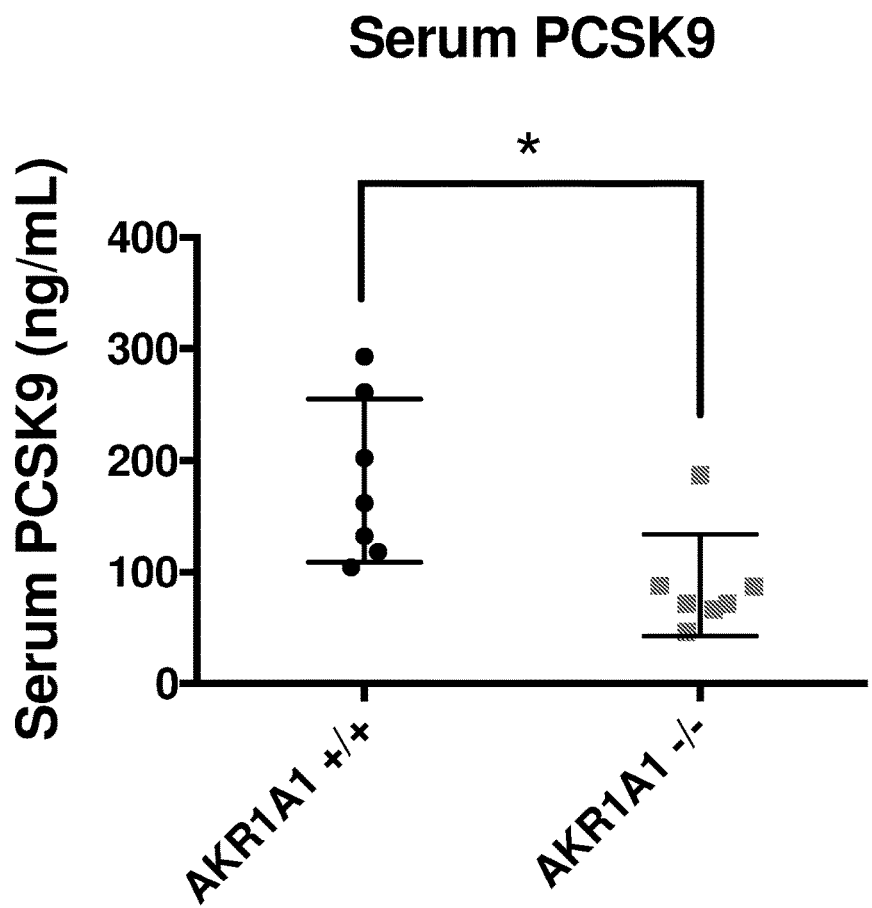
FIG. 4 illustrates a graph showing serum PCSK9 levels in AKR1A1 deficient mice.

FIG. 4 illustrates plots showing serum PCSK9 levels in AKR1A1 deficient 24-week old male mice and to 24-week old wild type mice. AKR1A1 deficient 24-week old male mice had reduced PCSK9 levels compared to 24-week old wild type mice.

Figure 5:
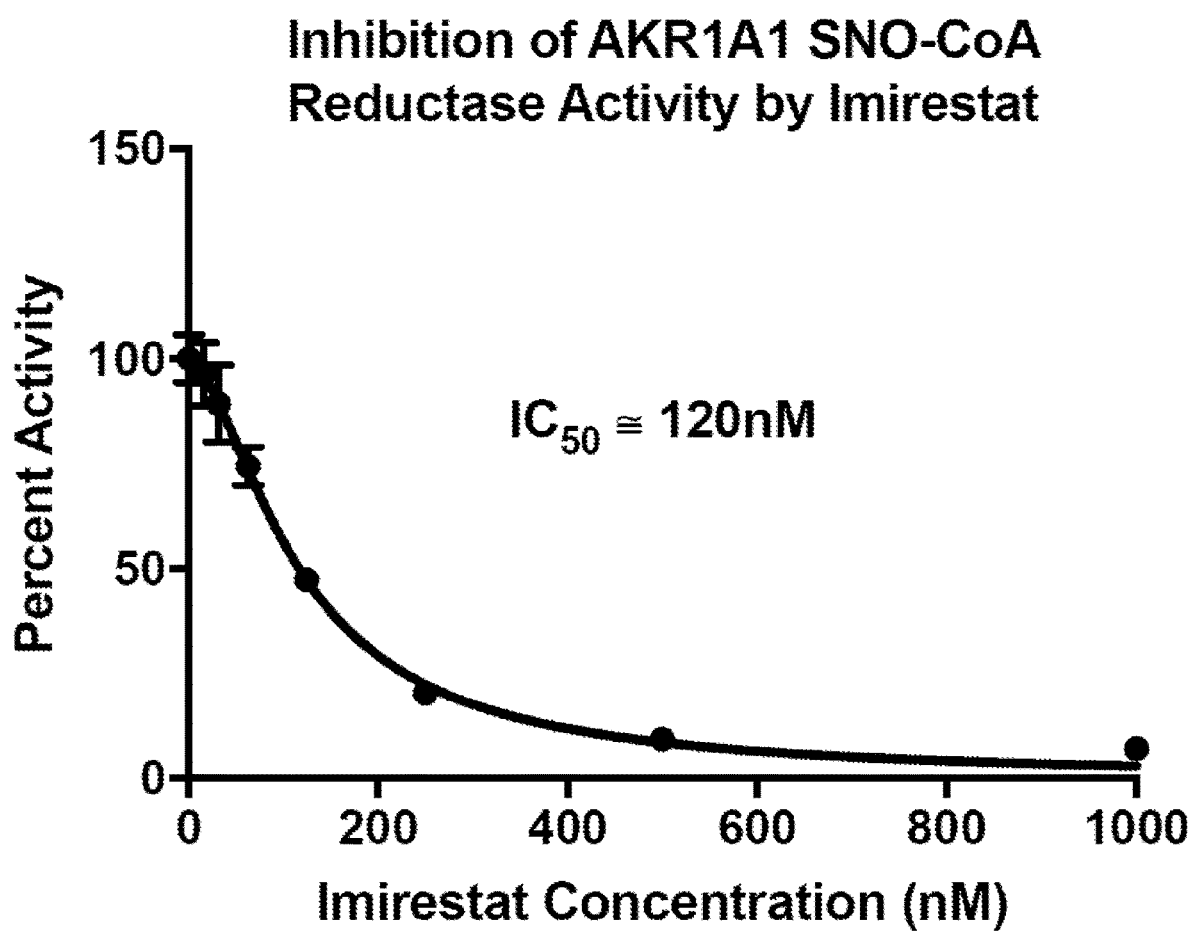
FIG. 5 illustrates a graph showing inhibition of AKR1A1 SNO-CoA reductase activity by Imirestat.

FIG. 5 illustrates a plot showing inhibition of AKR1A1 SNO-CoA reductase activity by Imirestat. The IC$_{50}$ for in inhibition of AKR1A1 SNO-CoA Reductase Activity by Imirestat was about 120 nm.

Figure 6:
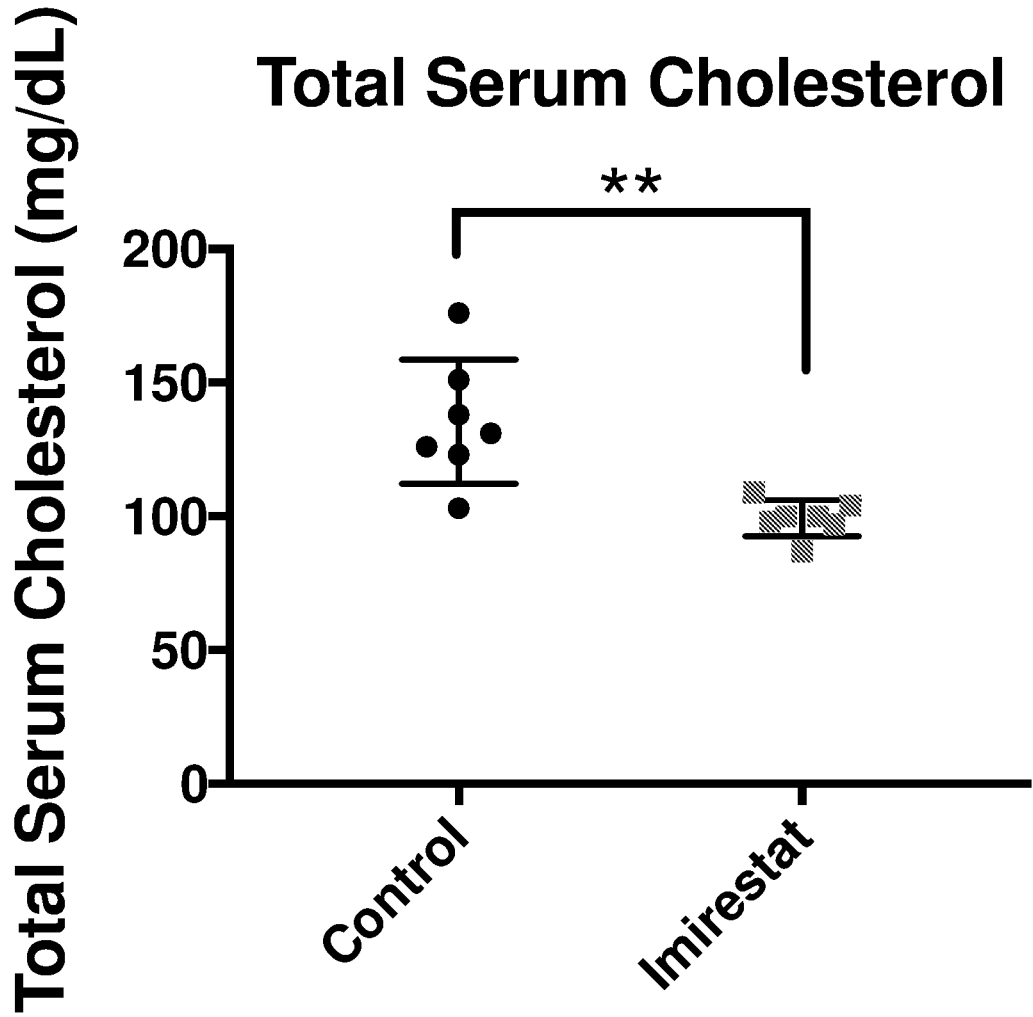
FIG. 6 illustrates a graph showing total serum cholesterol levels in mice treated with Imirestat.

FIG. 6 illustrates plots showing total serum cholesterol levels in C57BL6J 24 week old male mice treated for 4 weeks with-in diet Imirestat compared to control. The 24 week old male mice treated with Imirestat displayed lower total serum cholesterol than control 24 week old male mice.

Figure 7:
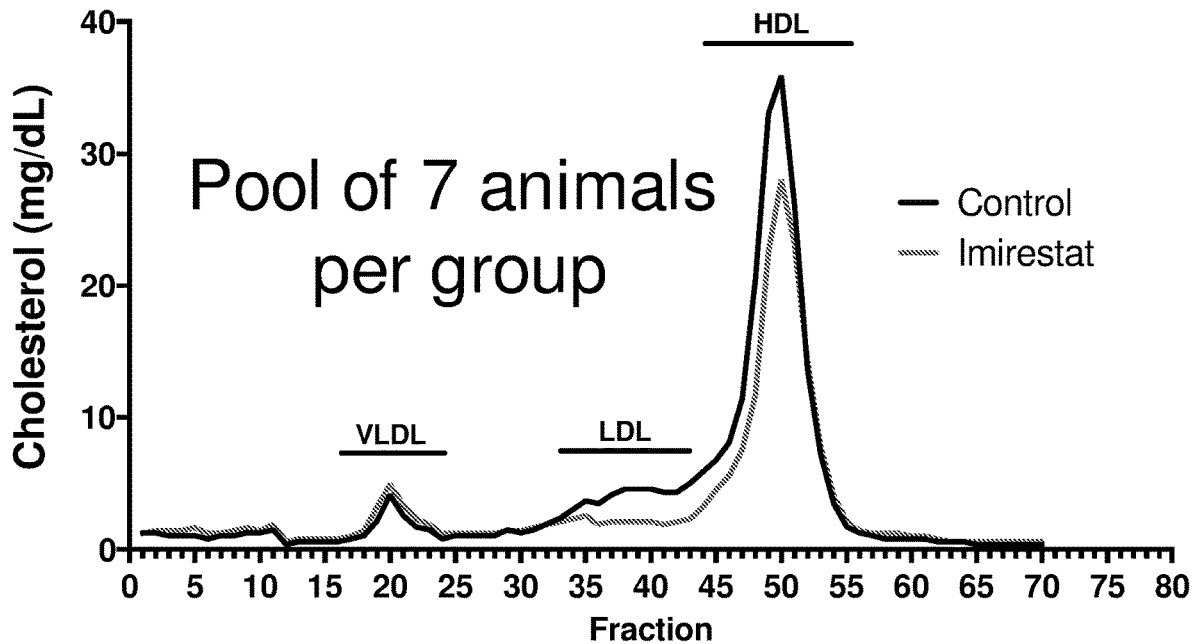
FIG. 7 illustrates a plot showing cholesterol fractionation in mice treated with Imirestat.

FIG. 7 illustrates a plot showing cholesterol fractionation in C57BL6J 24 week old male mice treated for 4 weeks with-in diet Imirestat compared to control. The cholesterol fractionation confirmed reduced total serum cholesterol in C57BL6J 24 week old male mice treated for 4 weeks with-in diet Imirestat compared to control 24 week old male mice.

Figure 8:
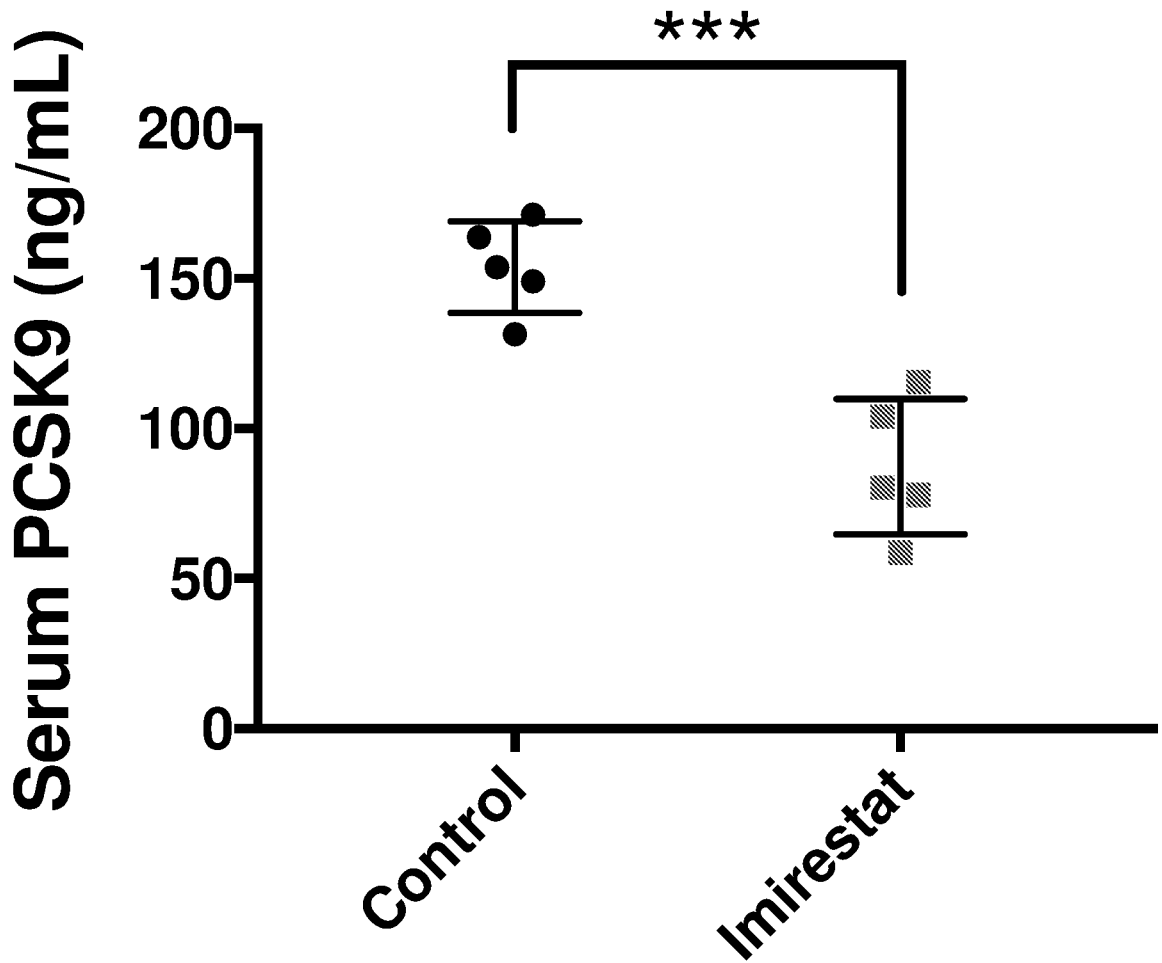
FIG. 8 illustrates a graph showing serum PCSK9 levels in mice treated with Imirestat.

FIG. 8 illustrates plots showing serum PCSK9 levels in C57BL6J 24 week old male mice treated for 4 weeks with-in diet Imirestat compared to control. The 24 week old male mice treated with Imirestat displayed lower total serum PCSK9 levels than control 24 week old male mice.

Figure 9:
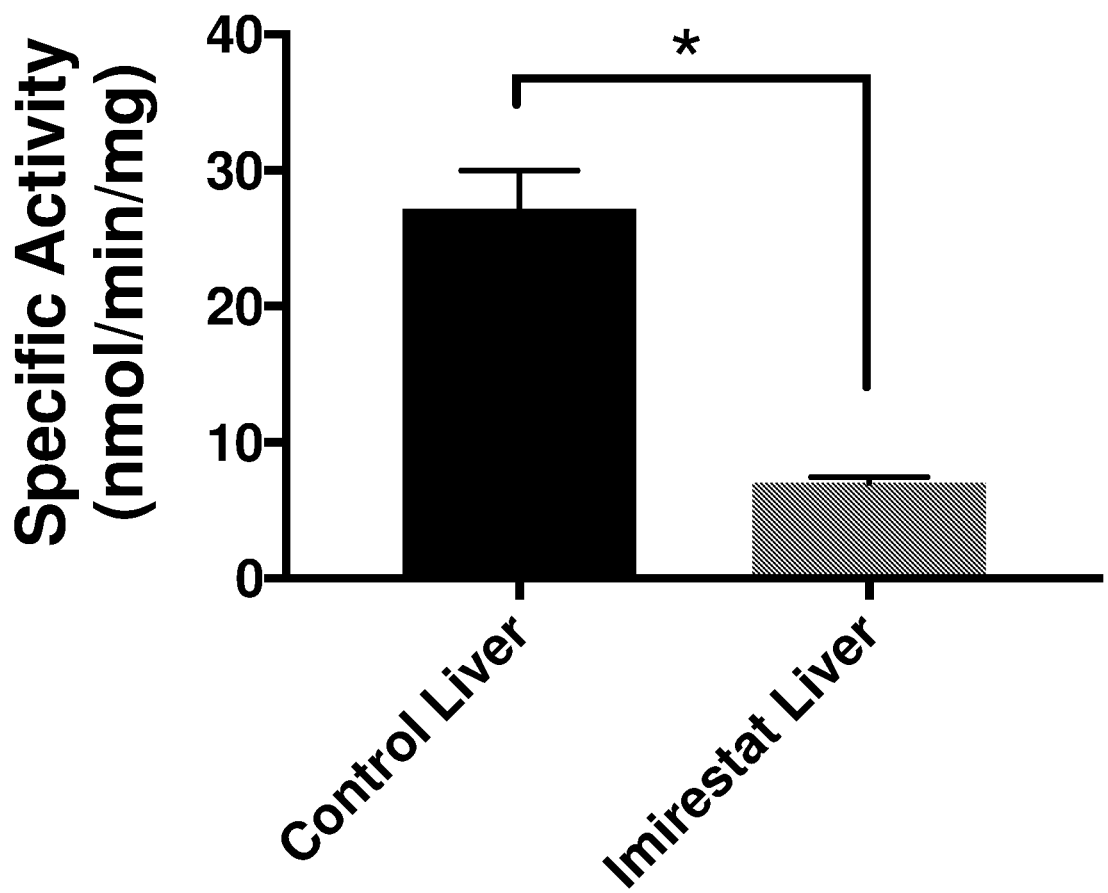
FIG. 9 illustrates a graph showing SnO-CoA Reductase Activity in mice treated with Imirestat.

FIG. 9 illustrates a graph showing SNO-CoA Reductase activity in liver in C57BL6J 24 week old male mice treated for 4 weeks with-in diet Imirestat compared to control. The 24 week old male mice treated with Imirestat displayed lower AKR1A1 liver activity than control 24 week old male mice.

Figure 10:
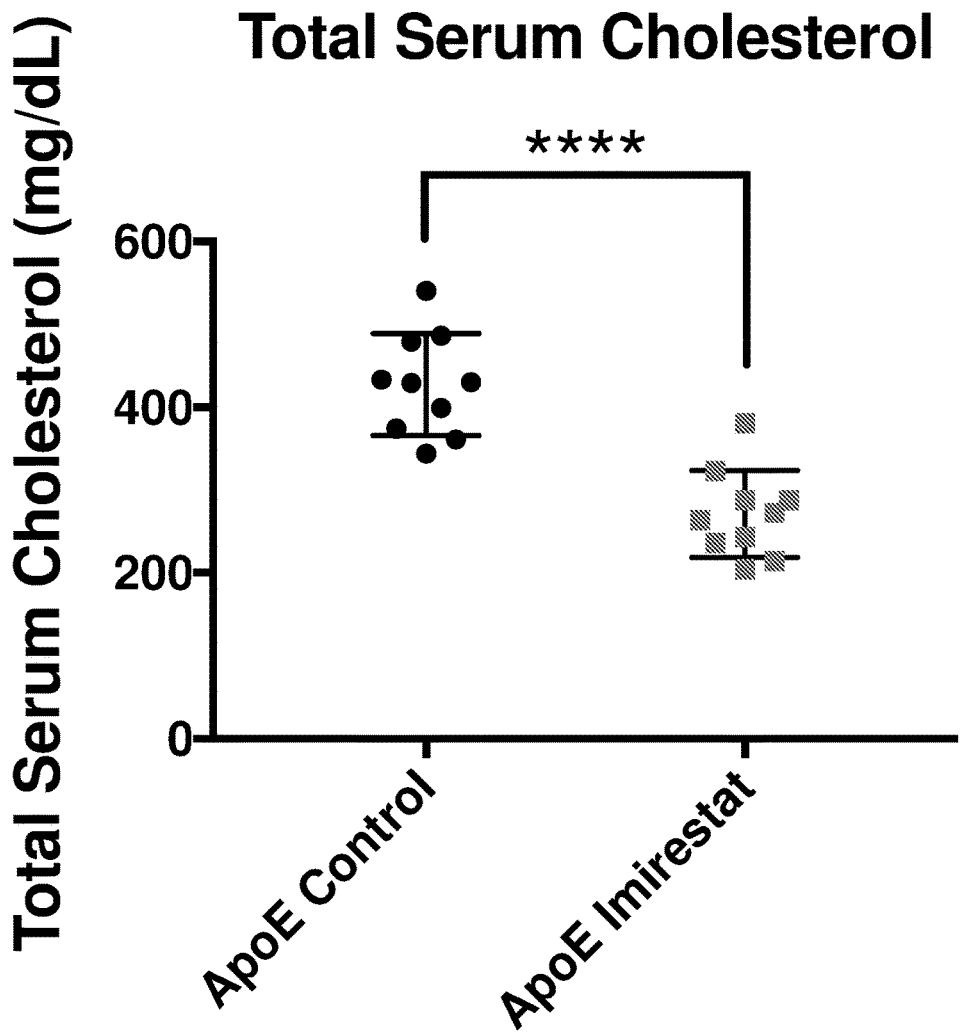
FIG. 10 illustrates a graph showing total serum cholesterol in ApoE-deficient mice treated with Imirestat.

FIG. 10 illustrates plots showing total serum cholesterol levels in ApoE deficient 24 week old male mice treated for 4 weeks with-in diet Imirestat compared to control. The 24 week old male mice treated with Imirestat displayed lower total serum cholesterol than control 24 week old male mice.

Figure 11:
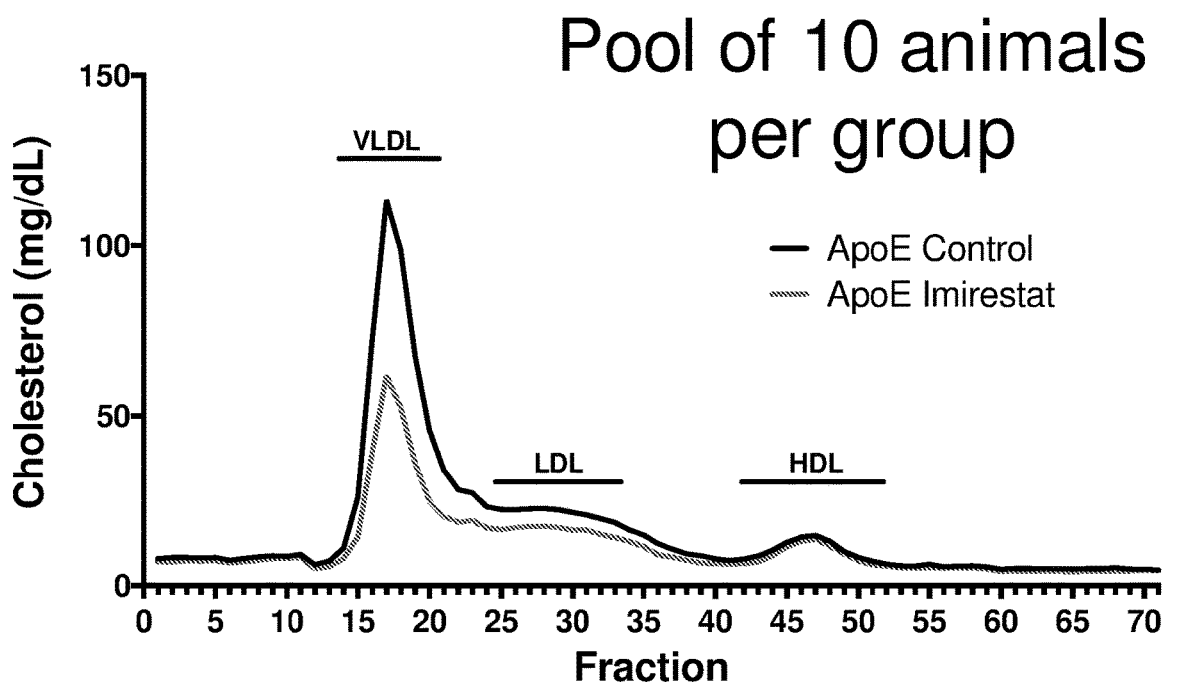
FIG. 11 illustrates plots showing cholesterol fractionation in ApoE-deficient mice treated with Imirestat.

FIG. 11 a plot showing cholesterol fractionation in ApoE deficient 24 week old male mice treated for 4 weeks with-in diet Imirestat compared to control. The cholesterol fractionation confirmed reduced total serum cholesterol in ApoE deficient 24 week old male mice treated for 4 weeks with-in diet Imirestat compared to control 24 week old male mice.

Figure 12:
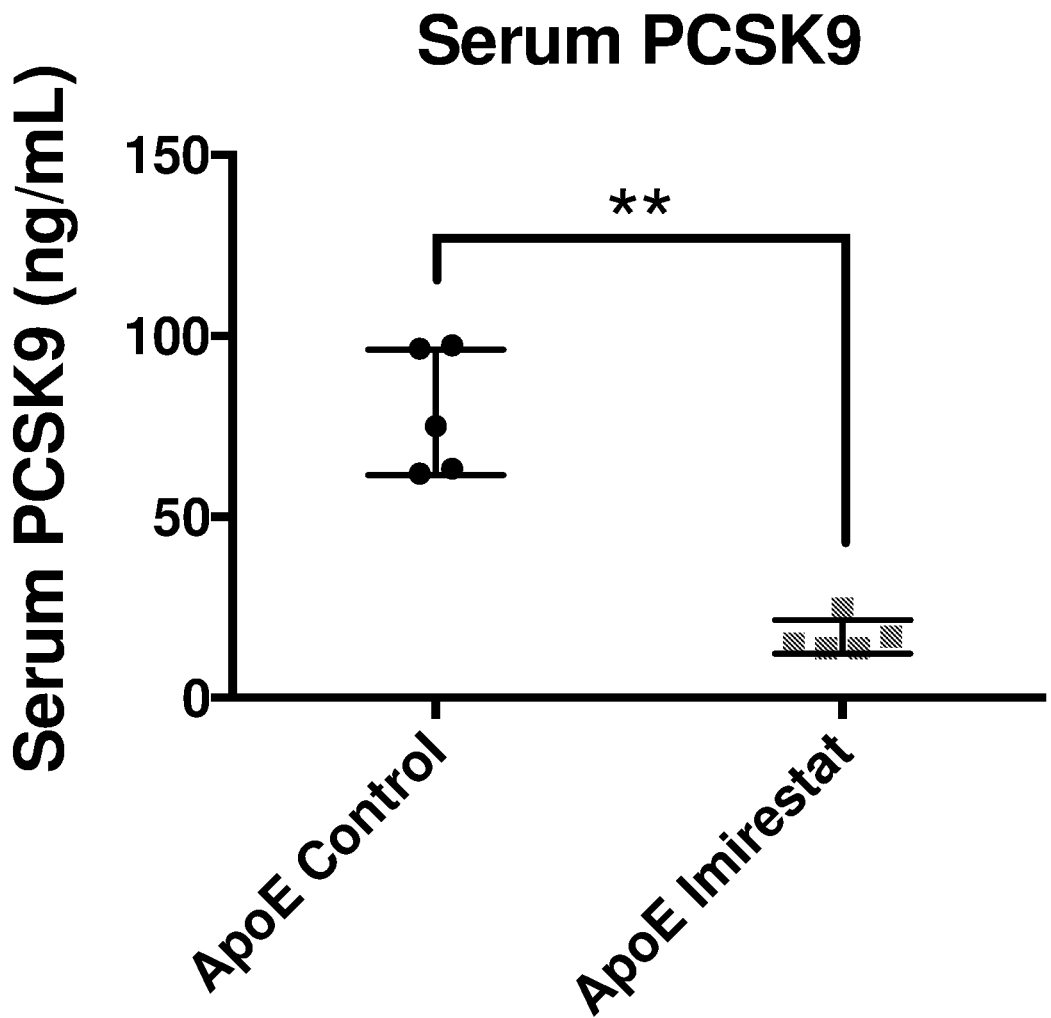
FIG. 12 illustrates a graph showing total serum PCSK9 levels in ApoE-deficient mice treated with Imirestat.

FIG. 12 plots showing serum PCSK9 levels in ApoE deficient 24 week old male mice treated for 4 weeks with-in diet Imirestat compared to control. The 24 week old male mice treated with Imirestat displayed lower total serum PCSK9 levels than control 24 week old male mice.

Figure 13:
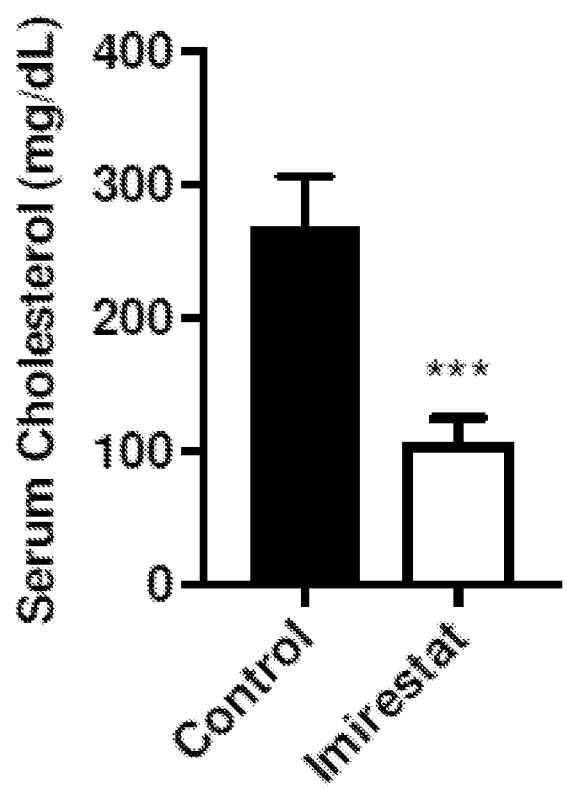
FIG. 13 illustrates a graph showing total serum cholesterol in CETP/ApoB100 transgenic (humanized) mice treated with Imirestat.
Figure 14:
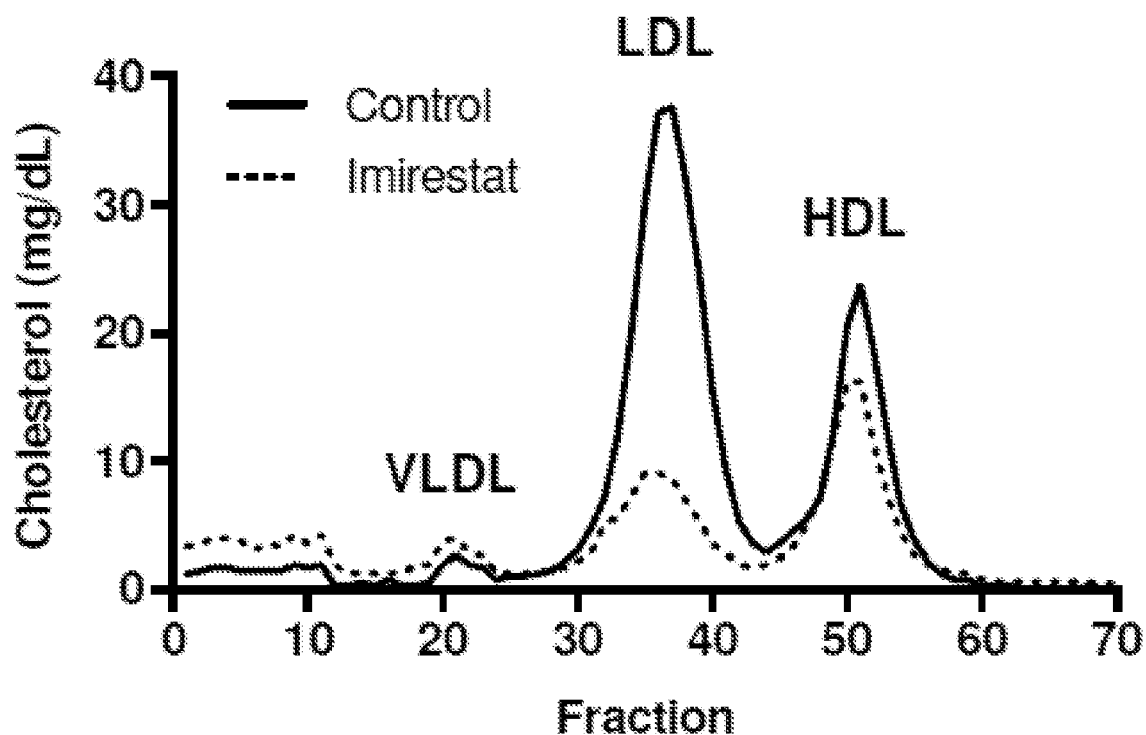
FIG. 14 illustrates a plot showing cholesterol fractionation in CETP/ApoB100 transgenic (humanized) mice treated with Imirestat.

FIG. 13 illustrates plots showing total serum cholesterol levels in CETP/ApoB100 transgenic 24 week old male mice treated for 4 weeks with-in diet Imirestat compared to control. The 24 week old male mice treated with Imirestat displayed lower total serum cholesterol than control 24 week old male mice.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, I claim:

1. A method of lowering serum cholesterol and/or PCSK9 levels in a subject in need thereof, the method comprising:

administering to the subject an AKR1A1 inhibitor at an amount effective to reduce serum cholesterol and/or PCSK9 levels, wherein the AKR1A1 inhibitor is 2,7-Difluoro-2'H,5'H-spiro[fluorene-9,4'-imidazolidine]-2',5'-dione (imirestat) or an analogue compound thereof selected from the group consisting of:
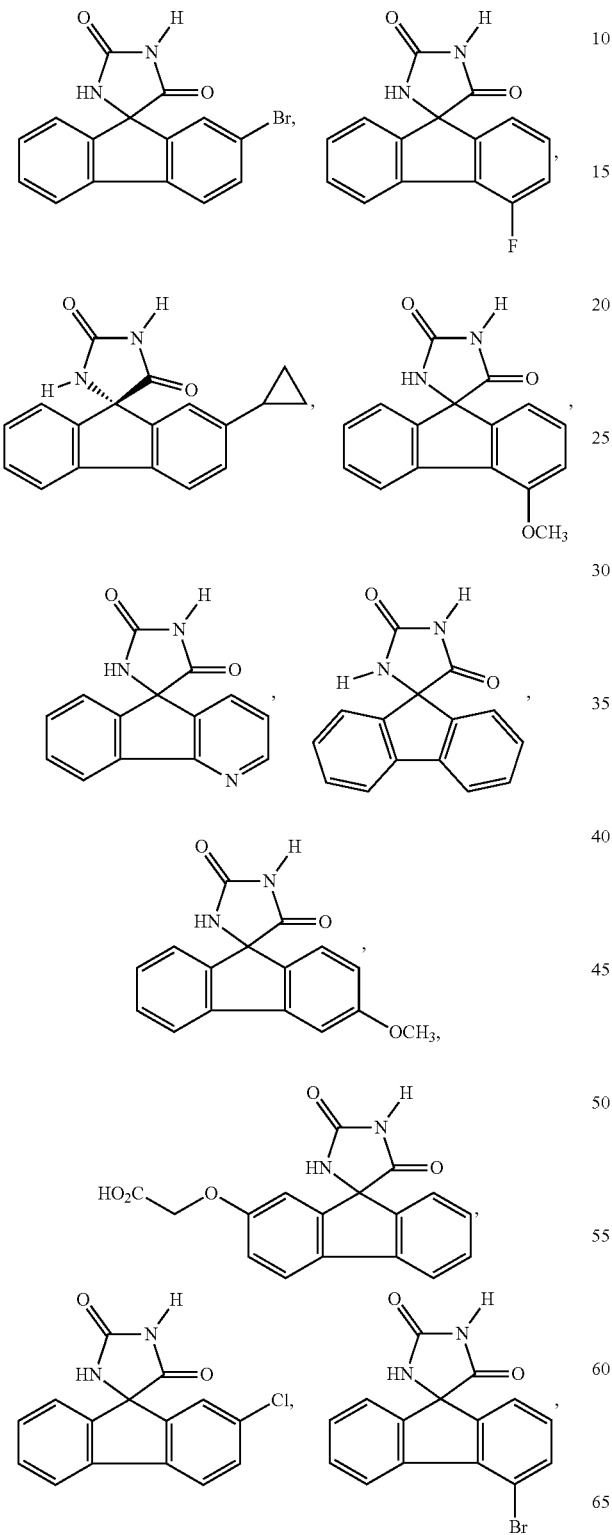
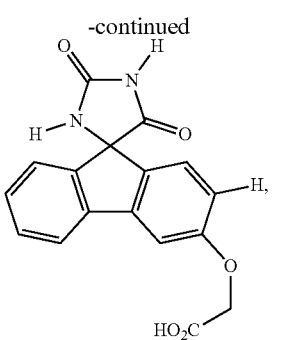
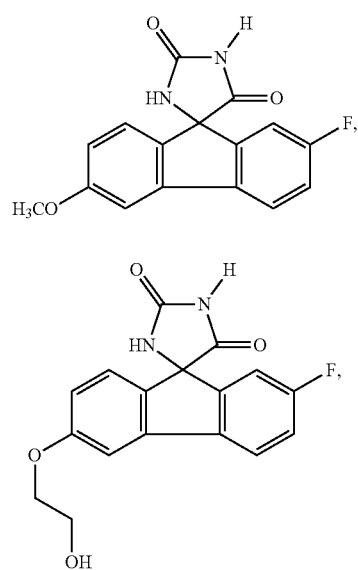
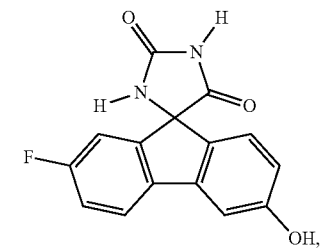
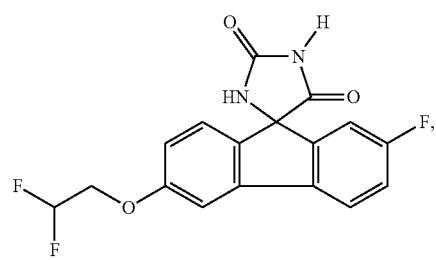
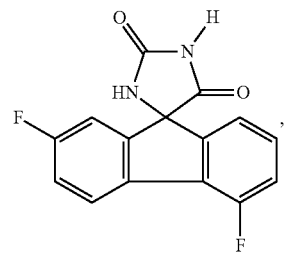

-continued

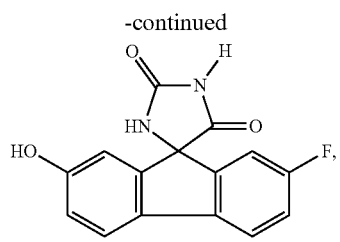
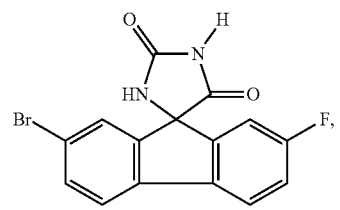
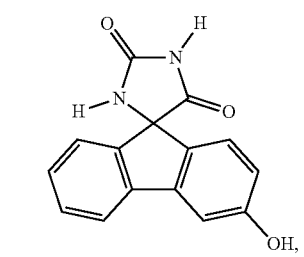
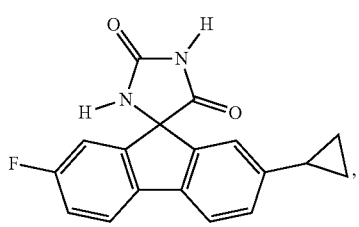
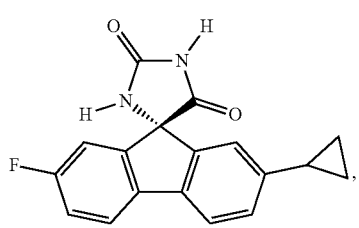
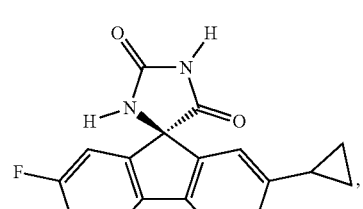
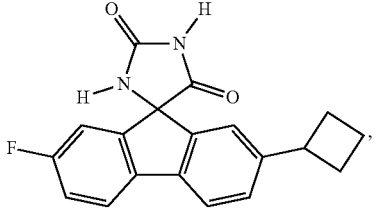

-continued

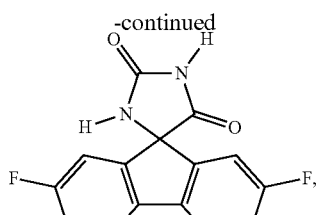
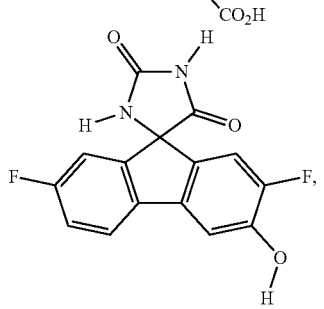
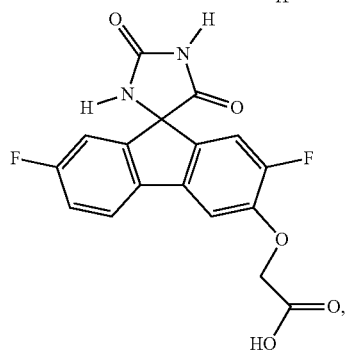
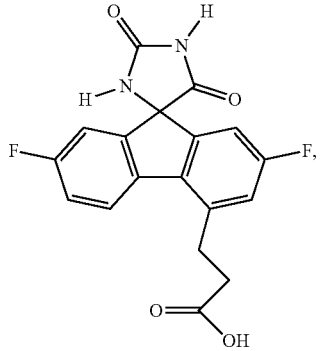

and pharmaceutically acceptable salts thereof.

2. The method of claim 1, wherein the AKR1A1 inhibitor administered to the subject: (i) reduces total serum cholesterol by at least about 5% relative to predose level; (ii) reduces serum LDL-C at least about 5% relative to predose level; (iii) reduces serum triglyceride at least about 5% relative to predose level; and/or (iv) not reduce serum HDL-C or reduces serum HDL-C no more than about 5% relative to predose level.

3. The method of claim 1, wherein the AKR1A1 inhibitor administered to the subject does not lower or do not substantially lower HDL-C levels.

4. The method of claim 1, wherein the AKR1A1 inhibitor does not result in accumulation of lipids in subject's liver.

5. The method of claim 1, wherein the AKR1A1 inhibitor includes 2,7-Difluoro-2'H,5'H-spiro[fluorene-9,4'-imidazolidine]-2',5'-dione (imirestat) and analogues thereof.

6. The method claim 1, wherein the AKR1A1 inhibitor can have a selectivity for AKR1A1 versus AKR1B1≥2 times.

7. The method of claim 1, wherein the subject has or is at risk of diabetes.

8. The method of claim 1, wherein AKR1A1 inhibitor is administered in combination with a selective or partially selective AKR1B1 inhibitor.

9. The method of clam 8, wherein the AKR1B1 inhibitor can have a selectivity for AKR1B1 versus AKR1A1≥2 times.

\* \* \* \* \*